(12) United States Patent
Lindo et al.

(10) Patent No.: US 10,744,254 B1
(45) Date of Patent: Aug. 18, 2020

(54) AUTOMATED PERITONEAL DIALYSIS DEVICE

(71) Applicant: Simergent, LLC, Oklahoma City, OK (US)

(72) Inventors: Steve Lindo, Chicago, IL (US); Richard Pendergraft, Norman, OK (US); Jennifer Miller, Rock Hill, SC (US); Jacob Henderson, Oklahoma City, OK (US); Trevor Roach, Oklahoma City, OK (US); Emily Byrne, Minneapolis, MN (US); Cameron Eckert, Markle, IN (US)

( * ) Notice: Subject to any disclaimer, the term of this patent is extended or adjusted under 35 U.S.C. 154(b) by 0 days.

(21) Appl. No.: 16/521,758

(22) Filed: Jul. 25, 2019

Related U.S. Application Data

(60) Provisional application No. 62/807,121, filed on Feb. 18, 2019.

(51) Int. Cl.
*A61M 1/28* (2006.01)
*A61M 1/16* (2006.01)

(52) U.S. Cl.
CPC ............ *A61M 1/284* (2014.02); *A61M 1/285* (2013.01); *A61M 1/287* (2013.01); *A61M 1/166* (2014.02); *A61M 1/1623* (2014.02); *A61M 1/288* (2014.02); *A61M 2205/52* (2013.01)

(58) Field of Classification Search
CPC ...... A61M 1/284; A61M 1/285; A61M 1/287; A61M 1/166
See application file for complete search history.

(56) References Cited

U.S. PATENT DOCUMENTS

| | | | | |
|---|---|---|---|---|
| 4,821,996 A * | 4/1989 | Bellotti | ............... | A61M 39/223 251/230 |
| 5,127,393 A * | 7/1992 | McFarlin | ........... | A61B 1/00154 600/114 |
| 5,722,947 A * | 3/1998 | Jeppsson | ................. | A61M 1/28 604/29 |
| 8,226,595 B2 * | 7/2012 | Childers | ............. | A61M 1/0023 604/29 |
| 8,852,167 B2 * | 10/2014 | Trombley, III | ....... | A61M 39/10 604/533 |
| 2013/0041317 A1 * | 2/2013 | Walter | .................... | A61M 5/44 604/114 |

* cited by examiner

*Primary Examiner* — Bradley J Osinski
(74) *Attorney, Agent, or Firm* — Richards Patent Law P.C.

(57) ABSTRACT

An automated peritoneal dialysis (APD) system using gravity to deliver fluid from one or more source dialysate bags to the patient as the destination, and using gravity to deliver fluid from the source patient to the destination drain container or drain receptacle, and heats at least one dialysate bag placed onto a heated plate, and using a disposable tubing set is used for dialysate delivery to and from the patient, and using one or more solenoid-operated, normally closed, electronically-controlled pinch valves which pinch or release the disposable tubing set's tubing to stop or start fluid flow, respectively.

20 Claims, 25 Drawing Sheets

AUTOMATED PERITONEAL DIALYSIS DEVICE

CROSS-REFERENCE TO RELATED APPLICATIONS

This application incorporates by reference and claims the benefit of priority to U.S. Provisional Application No. 62/807,121 filed on Feb. 18, 2019.

BACKGROUND OF THE DESCRIPTION

The present subject matter relates generally to automated peritoneal dialysis (APD) devices, and potentially may be applied to other medical device applications as well, including hemodialysis applications.

Peritoneal dialysis (PD) consists of a series of cycles of filling, dwelling, and draining dialysate solution into and out of a patient's peritoneal cavity in their lower abdomen for patients with End Stage Renal Disease (ESRD). The solution is exchanged by connecting one or more dialysate solution bag(s) and associated disposable tubing to a transfer set with a shutoff pinch valve, which in turn connects to a PD catheter surgically implanted in the patient's abdomen as shown in FIG. 5. PD dialysate solution contains dextrose, icodextrin (i.e., starch-derived glucose polymer), or other molecules to create an osmotic gradient which allows toxins and excess fluids in the bloodstream to transport through the peritoneal membrane's capillary walls and into the dialysate solution. PD dialysate solution also contains electrolytes to maintain patients' normal blood composition. PD dialysate solution is currently commercially available in three different dextrose concentrations and a single icodextrin concentration.

PD therapy is performed either via gravity with dialysate bag(s) hung on a pole or elevated shelf, or with a device (cycler) to provide the motive fluid pressure/suction, also known as Automated Peritoneal Dialysis (APD). APD therapy is typically performed for 8-10 hours each night while the patient sleeps. Dialysate bags are typically hung or placed at the beginning of therapy and are typically removed after therapy completion. The patient and/or a family member or caregiver typically sets up the APD device, its associated disposable tubing set, and PD dialysate bags each night before commencing therapy.

Today, active pumping APD devices are expensive, with significant costs associated with the pump, valves, pressure sensors, and/or pneumatic manifolds, along with significant costs associated with the disposable tubing sets with cassettes to interface with said APD devices. Additionally, excessive delivery and/or suction pressures causes inflow or outflow pain during filling or draining phases for many patients. For both of those reasons, gravity-based APD devices offer benefits over current active pumping APD devices.

Today, active pumping APD devices' disposable tubing sets with cassettes are expensive. Some cassettes may require expensive ultrasonic welding or other technology to bond a rigid plastic cassette with a flexible thin plastic sheeting membrane, with costly high scrap rates associated with failed sheeting bonds. An APD device's disposable tubing set without a cassette offers cost benefits over traditional cassette-based tubing sets.

A common, serious complication of APD therapy is peritonitis. Peritonitis can occur if a patient touches the fluid path of their disposable tubing set and/or solution bag access port, resulting in touch contamination. Touch contamination can introduce bacteria or other contaminants into the sterile fluid path, thus causing an infection or inflammation of the peritoneum, known as peritonitis. Accordingly, there is a need for technology to prevent touch contamination and thus reduce the likelihood of peritonitis. Some currently available APD solution bags offer a shrouded male Luer fitting on the bag's access port to reduce the likelihood of touch contamination for APD tubing sets. However, there are no shrouded female Luer fittings which mate to the dialysate bags' shrouded male Luer fittings. Typical female Luer fittings have exposed fluid paths.

An APD device's disposable tubing set without a cassette poses a potential problem with the user loading the tubing into the hardware enclosure in the reverse orientation. Accordingly, there is a need for features to prevent the tubing set from being loaded in the reverse, upside down, backwards, or other incorrect orientation into the hardware enclosure using one or more simple, inexpensive, molded plastic parts and without requiring the usage of an expensive cassette and its associated bonded flexible membrane(s) described in the previous paragraph.

Conventionally, active pumping APD device systems, when combined with the requisite dialysate bags, are oriented in a horizontal fashion when set up in the patient's home. The APD device is typically placed on a stationary nightstand or large cart, with one or more PD dialysate bags placed next to the APD device to achieve the typical 10,000 mL-15,000 mL delivery volumes via multiple bags, each typically ranging in volume from 2,000 mL to 6,000 mL. A typical configuration might be one 5,000 mL bag placed on the APD device as a heater bag, one additional 5,000 mL bag (supply bag) placed next to the APD device, and another 2,000 mL bag (last fill bag) also placed next to the APD device. An APD device with integrated wheels and vertically-oriented dialysate bag mounting structure provides mobility benefits over current active pumping APD devices because the entire system takes up a smaller footprint on the floor and is thus more easily transported throughout the patient's home than active pumping devices mounted on a nightstand or large cart.

Patients and health care providers may desire for APD devices to be portable, both within the home and outside the home. For gravity-based devices, portability poses a problem since the machines tend to be rather tall in their therapy operational position.

Free flow of fluid from an APD device resulting in unintended Increased Intraperitoneal Volume (IIPV) can be fatal to patients. As such, there is a need for mechanisms to prevent free flow during certain single-fault conditions, such as loss of power to one or more valves which control fluid flow to or from the patient.

Conventionally, APD devices are often audibly noisy during operation. They are also prone to fluid ingress. As such, an APD device with a door over the pinch valves offers benefits over devices without said door because the door muffles the clicking noise from pinch valve actuation and provides fluid ingress protection to the pinch valves and internal components behind the pinch valve mounting wall.

Conventionally dialysate bags are often difficult to lift up to place them in the proper position required for therapy. Dialysate bag volumes may reach or exceed 6000 ml, with corresponding weights of approximately 61 Newtons (13.7 lb). These bags typically must be lifted from their original shipping container(s) (e.g. cardboard box) from approximately ground level to either approximately waist height for active pumping APD devices, or from ground level to 1.2-1.9 meters above ground level for gravity-based APD devices, in order to achieve the necessary head height required for appropriate therapeutic flow rates. In addition, the peritoneal dialysis patient population tends to skew older and more frail than the general population, thus exacerbating these potential lifting difficulties. Lifting heavy dialysate bags may cause shoulder or back problems, may lead to the user losing balance and/or falling over. These same difficulties may be experienced by caregivers who may perform setup rather than the patients themselves. Additionally, patients and caregivers in certain regions in the globe and/or female patients may have smaller statures and may not have as much strength as others. Additionally, many PD patients also suffer from other comorbidities or illnesses such as diabetes mellitus, which may further reduce the patient's ability to lift heavy objects.

Conventionally there have been no APD devices which assist the patient or caregiver in lifting PD dialysate solution bags. Existing APD devices do not provide any sort of mechanical advantage nor any other active or passive features to assist patients or caregivers in lifting heavy bags to the proper height required to perform APD therapy. As such, some physicians may be hesitant to prescribe APD therapy to a patient they believe may not possess the strength to lift the bags into place. Those patients may be forced to perform hemodialysis instead, which may not be the preferred dialysis modality for those patients.

Some manufacturers may instruct patients to use several smaller dialysate bags (e.g. 2000-2500 ml each) rather than fewer larger bags (5000-6000 ml each) for ease of lifting. However, several smaller bags are more expensive to manufacture than fewer larger bags. Additionally, several smaller bags may take up more room on the surface on which the bags are placed (e.g. table, cart, nightstand, etc).

APD patients may use different dialysate fluid concentrations within a given therapy, or from one therapy to the next. One existing APD device simply says, "CONNECT BAGS", rather than helping identify which bag to connect to which disposable tubing set connector. In addition, although physicians and nurses may think of the bags in terms of the concentration of the osmotic agent, (e.g. dextrose concentration), patients may think of the bags in terms of the color of the bag connector associated with a given concentration, which may also correspond to the color of the tape securing the top of each dialysate box. Currently available color/concentration combinations include Yellow (1.5% dextrose), Green (2.5% dextrose), Red (4.25% dextrose), or Purple (7.5% icodextrin).

APD patients and/or their caregivers may be illiterate or have low literacy. They may not be able to read text-based prompts to properly set up, monitor, tear down, or troubleshoot their APD therapy.

Some manufacturers have attempted to mitigate the height required to lift the bags for gravity-based APD therapy by placing the bag hooks/shelves at a lower height than they would otherwise want to place them to achieve good flow rates. These approaches may be used for either active pumping or gravity-based APD devices.

If a gravity-based APD device provides a lower-than-optimal placement height for the dialysate bags, the flow rates for delivering fresh dialysate solution to the patient may be reduced. This will either result in a longer therapy duration or less effective therapeutic outcomes.

A PD therapy consists of several cycles of fill, dwell, and drain. The exchange of toxins and excess fluid from the patient's bloodstream occurs primarily during the dwell periods. If it takes longer to fill due to suboptimal dialysate bag head height, then there may be less time available for dwelling. Diffusion and osmosis occurs between the patient's peritoneal membrane and the solution dwelling in contact with that membrane, after having been filled from the APD device. Therefore, therapy is less effective if low flow rates result in less dwell time, for a given (e.g. 8 hour) total therapy time. Alternatively, low flow rates could lead to longer total therapy duration, which is not desirable since patients' lives are disrupted with therapy durations that exceed the patient's normal nocturnal sleep duration.

In some locations, AC power outages are a frequent occurrence, each potentially lasting several hours. Other locations may have frequent, short duration AC power outages and/or brownouts, each lasting a few seconds or several minutes.

Additionally, if patients want to start therapy in one room within their home while performing some activity (e.g. watching TV, cooking, studying, etc), followed by movement to their bedroom to complete therapy, there may not be AC plugs readily available in all of the locations within the home that patients may find themselves wanting to perform some or all of their APD therapy.

To date, no commercially available APD device is able to continue delivering therapy during an AC power outage.

Currently, none of the widely available, inexpensive pinch valves are capable of opening the pincher jaws if a tube is not already installed in the valve, using the manufacturer's recommended voltage. They are only able to open the pincher jaws when the solenoid is activated with a tube already installed. If the solenoid is activated via its nominal specified voltage without a tube installed, the pinch valve jaws do not open. For an APD device to use pinch valves, it is desirable for the pinch valves to open when commanded by the software, even if no tube is installed, in order to facilitate loading the tubing set into the pincher jaws. There is also a need to open the pinch valves during AC power outages. Accordingly, there is a need for opening pinch valves without tubing installed, while using a commonly available, affordable battery.

Current APD devices offer an option to drain the spent effluent into a disposable drain container, typically constructed of flexible plastic film with inlet and/or outlet ports bonded into the bag. There is a need for a reusable drain container which is not frequently discarded to reduce cost and improve the environmental impact of the extra plastic drain container typically discarded each day.

Additionally, APD users may have difficulty draining the relatively large fluid volumes that may be stored in one or more reusable or disposable drain containers if the drain containers do not contain features to facilitate easy drainage.

Some physicians will deliver to the nurse or patient a prescription written in terms of total therapy volume (Total Therapy method), thus leaving the nurse, patient, and/or APD cycler to perform the math to calculate how many cycles will be delivered. Other physicians may write a prescription in terms of number of cycles (Number of Cycles method), leaving the nurse, patient, and/or APD cycler to calculate the total therapy volume, based on the cycle fill volume and optional last fill volume.

Also, some physicians write a prescription in terms of total therapy duration (Total Therapy method), leaving the nurse, patient, and/or APD cycler to perform the math to calculate the dwell duration per cycle. Other physicians may write a prescription in terms of dwell time per cycle, leaving the nurse, patient, and/or APD cycler to perform the math to calculate the total therapy duration, based on the cycle dwell time, total volume to be filled and drained, and the estimated flow rates for filling and draining.

Some conventionally available APD cyclers only allow prescription programming via the Total Therapy method. At least one existing APD cycler allows programming via either the Total Therapy method or the Number of Cycles method, but it requires the user to choose which method they will use prior to prescription programming. Users may not know which method they need to use, which could result in selecting the wrong programming method, attempting to enter their prescribed parameters, only to later realize the user interface doesn't have the programmable option(s) they need, thus resulting in the user backing out from the programming menu and trying to program the prescription again using the alternate programming method. Users prefer to simply enter whatever information they were given by their physician or nurse, without having to select from Number of Cycles method vs. Total Therapy method.

Patients and health care providers desire for APD devices to be portable, affordable, easy to clean, and aesthetically pleasing. Accordingly, there is a need for a system that addresses problems associated with active pumping devices, APD cassettes, peritonitis, loading tubing sets, horizontal device footprint, portability, free flow/IIPV, noise, dialysate bag lifting problems, connecting the proper bag concentration, low literacy users, low flow rates, therapy efficacy, AC power outages, opening pinch valves, draining spent effluent, and therapy programming, while providing a cost effective means to deliver good dialysate flow rates with accurate volumetric measurement to encourage fast fill cycles, resulting in a safe, efficient and effective therapy.

BRIEF SUMMARY OF THE INVENTION

To meet the needs described above and others, the present disclosure provides multiple solutions to the problems of peritonitis, active pumping devices, APD cassettes, loading tubing sets, horizontal device footprint, free flow/IIPV, noise, dialysate bag lifting problems, connecting the proper bag concentration, low flow rates, therapy efficacy, portability, drain containers, and therapy programming to encourage easy disposables setup, and prevent unnecessary injuries.

In satisfaction of this and related objects, the present system provides an improved automated peritoneal dialysis device which is unique in its design, manufacturability, and its capacity to serve as an automated peritoneal dialysis device in a cost-effective manner.

An automated peritoneal dialysis (APD) system using gravity to deliver fluid from one or more source dialysate bags to the patient as the destination, and using gravity to deliver fluid from the source patient to the destination drain container or drain receptacle, and heats at least one dialysate bag placed onto a heated plate, and using a disposable tubing set for dialysate delivery to and from the patient, and using one or more solenoid-operated, normally closed, electronically-controlled pinch valves which pinch or release the disposable tubing set's tubing to stop or start fluid flow, respectively.

The system can include a heater bag that can be heated via a heater element separated from a metal heater plate by a layer of flexible rubber and one or more layers of electrically insulated polyamide film.

The system can include one or more openable and closeable doors covering all or a portion of one or more pinch valves. The one or more of the doors can contain internal ribs or protrusions which contact or come very close to one or more of the disposable tubing set's tubes when the door is closed, and wherein one or more of the ribs are positioned close to a pinch valve such that the rib or protrusion prevents the tubing from coming dislodged from the pinch valve jaws. The system can include noise-reducing foam or other noise-reducing material is used inside the doors and outside of the one or more pinch valves. The noise-reducing foam can be used outside of the one or more pinch valve bodies around the valves' solenoid coil(s) housing.

The source dialysate bags may include a heated bag and a non-heated supply bag which may be replenished into the heated bag such that replenishment fluid flow is controlled via a dedicated Supply replenish pinch valve which is in turn controlled via a microcontroller. The supply bag may contain dextrose (or any suitable solution), commonly used for APD therapy.

An additional source dialysate bag may include a unique last fill bag which is replenished into the heater bag prior to delivery of the last fill before the patient is to disconnect from the system for the long daytime dwell period such that replenishment fluid flow is controlled via a dedicated Last Fill replenish pinch valve which is in turn controlled via a microcontroller. The additional last fill source dialysate bag may contain icodextrin (or any suitable solution), commonly used as the last fill solution in APD therapy.

The fluid flow from the heated bag to the patient is controlled via a dedicated Patient Fill pinch valve which is in turn controlled via a microcontroller. The fluid flow from the patient to the drain container or drain receptacle is controlled via a dedicated Patient Drain pinch valve which is in turn controlled via a microcontroller.

The fluid volume delivered from the heater bag to the patient can be calculated via weight using one or more load cells, and the fluid volume drained from the patient to the drain destination or drain container is calculated via weight using one or more load cells, wherein the output from all load cells are measured and stored by a microcontroller and its associated memory.

The therapy status information can be displayed via graphical touch screen and therapy programming and user input is entered via graphical touch screen. The therapy prescription may be programmed by the user via the touch screen such that the user may use the Total Therapy method wherein the user directly enters the total therapy volume, total therapy duration, cycle fill volume, and last fill volume, and the cycler calculates the number of cycles and the cycle dwell duration, and the user may use the Number of Cycles method wherein the user directly enters the number of cycles, cycle dwell duration, cycle fill volume, and last fill volume, and the cycler calculates the total therapy duration and total therapy volume, wherein the APD cycler automatically transitions from Total Therapy Method to Number of Cycles method if the user attempts to directly enter any one of the following: Number of Cycles, Cycle Dwell time, wherein the system automatically transitions from Number of Cycles method to Total Therapy Method if the user attempts to directly enter any one of the following: Total therapy duration, total therapy volume.

The user may also enter estimated total therapy ultrafiltration volume or estimated per-cycle ultrafiltration volume to assist in the calculation of cycle dwell duration for the total therapy method or to assist in the calculation of total therapy duration for the number of cycles method, and in either method, durations are adjusted based on the extra time required to drain the estimated ultrafiltration volume.

The one or more of the doors can contain one or more torsion springs to spring-load the door in the opened position. The one or more of the doors can contain one or more compression or tension springs to spring-load one or more door latches to the closed (latched) position. The one or more door position sensors can monitor the position of one or more of the doors via a microcontroller AND which cause an audible or visual alarm to be generated if one or more doors are opened during therapy.

The therapy prescription information or therapy results can be stored on a removable USB memory stick which may be inserted into the APD cycler. The user may program the APD cycler by inserting a USB memory stick which had been pre-programmed by the user's clinician. Additionally, the USB port may be connected to an external communication device, such as a wireless cellular modem or wired or wireless internet device.

The one or more enclosures can be mounted onto, or removable from, an IV pole via pole clamps, wherein the IV pole contains at least 3 wheels, wherein the IV pole contains a weighted base and/or wide enough wheelbase such as such an amount as to mechanically prevent the entire system's center of gravity from exceeding a horizontal distance beyond the center of the furthest wheel when placed at an angle of at least 10° from horizontal, when the maximum number of the maximum volume of permissible dialysate bags are loaded in their highest permissible height configuration and the drain container is empty. The dialysate bag (heater bag) may be placed onto the first enclosure which heats the bag to approximately body temperature as measured by one or more temperature sensors, wherein the first enclosure is mounted above the patient's bed surface, wherein at least a second enclosure contains a touch screen display wherein the second enclosure is mounted below the first enclosure, wherein a reusable drain container may be placed onto a third enclosure, which weighs the drain container via one or more load cells wherein the third enclosure is mounted below the second enclosure and below the patient's bed surface.

The one or more enclosures can be mounted onto a pole constructed of square or rectangular tubing with multiple holes along a vertical axis along one or more sides of the tubing, wherein one or more enclosure-holding platforms are each mounted to the pole via one or more removable pin(s) through the aforementioned holes to allow for adjustable height of the platform(s), wherein one or more of the enclosures mount to the enclosure platform(s), wherein the pole contains two fixed-axis wheels and one or more casters wherein the caster(s) have 360° rotation capability, wherein a dialysate bag (heater bag) may be placed onto the first enclosure which heats the bag to approximately body temperature, wherein the first enclosure is mounted above the patient's bed surface, wherein at least a second enclosure contains a touch screen display wherein the second enclosure is mounted below the first enclosure, wherein a reusable or disposable drain container may be placed onto a third enclosure, which weighs the drain container via one or more load cells wherein the third enclosure is mounted below the second enclosure and below the patient's bed surface.

The vertical scaffold (e.g., pole) can be constructed of two or more segments which may be disassembled for transport, wherein one or more of the enclosures may be removed from the pole, and wherein the pole can be removed from the base for transport. The one or more wheels or casters can be detachable from the pole assembly for transport. For example, the vertical scaffold can include a bottom pole that has a welded insert that can be concentric with a top pole that fits into the welded insert of the bottom pole (or vice versa). In an example, the majority of the length of the two or more poles are constructed of square tubing material.

The destination drain container can be a reusable plastic container, wherein the container can be transparent to allow the user to view the color and status of the spent effluent.

The drain container inlet hole can include a tubing clip that interfaces with the disposable tubing set to maintain an air gap between the distal end of the tubing set and the maximum permissible fluid volume in the drain container, wherein a control system closes the drain pinch valve if one or more load cells detect that the drain container has reached its maximum permissible fluid volume. The drain container can contain a spigot with a closable/openable valve. The drain container contains a vent hole wherein a closable/openable cap can be positioned over the vent hole.

The drain container can contain a flat side along the side closest to the drain spout opening such that the drain container may be tipped over approximately 90° such that it is resting on its flat side while the fluid contents are drained into a tub, toilet, sink, floor drain or other drain destination.

The destination drain container can be split into a primary and secondary drain container such that spent effluent flows from the disposable tubing set's drain line into the primary drain container, wherein when the primary drain container is filled to capacity, it spills spent effluent into a secondary drain container.

The disposable tubing set may not contain any thin flexible plastic sheeting which is intended to be depressed in either direction in order to pull fluid into a cassette, AND does not contain any thin flexible plastic sheeting intended to be depressed in either direction in order to push fluid to its destination, and does not contain any thin flexible plastic sheeting intended to be depressed in either direction to shut off fluid flow from any source to any destination.

An automated peritoneal dialysis (APD) system which delivers fluid from one or more source dialysate bags to the patient as the destination, wherein a disposable tubing set is used for dialysate delivery to and from the patient, wherein the disposable tubing set contains one or more connectors with a shroud around the fluid path wherein one or more of the connectors are intended to connect to a shrouded dialysate solution bag connector.

The disposable tubing set's solution line connectors can be shrouded connectors such as shrouded female Luer fittings and wherein they are intended to connect to dialysate solution bags which contain shrouded male Luer fittings, both of which may be of Luer connectors or other threaded connector. The genders may be swapped between bags and disposable set solution line connectors, and thread types other than Luer-style may also be envisioned.

The disposable tubing set can contain one or more two-way or three-way fittings, wherein each fitting contains a protrusion on one side of the fitting and not the opposite side, wherein the APD cycler's enclosure contains a groove or notch which serves as a female receptacle for the male groove or notch in the tubing set such that the asymmetrical fitting's protrusion fits into the groove or notch to reduce the likelihood of the user installing the fitting in the reverse orientation, wherein the fitting is intended to be installed next to one or more pinch valves.

The disposable tubing set can contain one or more fittings, wherein the fitting(s) contains a gusset on one side and no gusset on the opposite side, wherein the APD cycler's enclosure contains a protrusion in the region where the fitting is to be installed which would interfere with the gusset if the user attempts to install the in the reverse orientation, wherein the fitting is intended to be installed next to one or more pinch valves.

The one leg of the fitting can route fluid from a non-heated dialysate supply bag, another leg routes fluid to or from a heated dialysate bag. The optional third leg of the fitting can route fluid from a non-heated last fill dialysate bag, which is intended for delivery as a last fill bag for long daytime dwell and which may be of a different concentration than the heater bag.

In another location downstream from the fitting above, a second fitting is envisioned, which contains the same gusset and protrusion as described above, and which is mounted into a hardware enclosure containing the same features described above to prevent reverse loading. The one leg of the fitting can route fluid from a heated dialysate bag, another leg routes fluid to or from a patient, and a third leg routes fluid to a drain container or drain receptacle.

The APD cycler can have a graphical user interface with pictorial guidance on proper installation orientation of the custom fitting(s) into the hardware enclosure. The APD cycler can have a graphical user interface with pictorial guidance on proper installation orientation of the custom fitting(s) into the hardware enclosure.

A first custom fitting can be placed within the enclosure containing a heater element and a pinch valve connecting the non-heated supply bag to the heated bag, wherein a second custom fitting is placed within the enclosure containing the pinch valve connecting the heater bag to the patient and another pinch valve connecting the patient to the drain container or drain receptacle.

The first custom fitting can be colored similarly to the enclosure containing the heater element, wherein the second custom fitting is colored similarly to the enclosure containing the touch screen display, wherein the color of the first custom fitting is substantially different from the color of the second custom fitting.

The APD cycler's door can contain internal ribs or other similar features which would interfere with the gusset if the door is fully closed while the custom fitting is installed in the reverse (incorrect) orientation.

The system can be an automated peritoneal dialysis (APD) system or continuous ambulatory peritoneal dialysis (CAPD) system, hemodialysis system, IV infusion pump, or other medical fluid delivery system with solution bag lifting mechanism, the system including one or more valves to control fluid delivery routing from solution bag(s) to a patient via disposable set(s); and a lifting mechanism to assist the user in lifting one or more solution bag(s) from a lower height to a higher height.

The solution bag lifting mechanism can use a spring loaded reel and cable system, one or more gas springs or linear actuators, one or more spring-loaded hinges, one or more pulleys and one or more of the following: cable, string, rope, or belt, user-applied downward force, which may leverage the user's body weight, to direct one or more medical solution bags in an upward direction, and/or one or more electric motors.

The solution bag lifting mechanism can use one or more levers, one or more flexible straps whereby the user pulls on the strap(s) to raise the bag(s), one or more manual cranks, one or more screws mechanism, which could include a ball screw or lead screw or other screw, cam followers in conjunction with linear rail(s), and/or one or more linear motion traveling car(s) mounted on one or more linear rail(s), two or more telescoping rigid tubes. The one or more of the telescoping tubes can be spring-loaded.

The solution bag lifting mechanism can use a scissor lift mechanism, hydraulic or pneumatic pumping mechanisms, and/or one or more counterweights connected to the bag(s) via cable and pulley.

The present system can include an automated peritoneal dialysis device or hemodialysis device or other medical fluid delivery device that uses colored or patterned graphical icons or unique colored or patterned combinations on the user interface to indicate the solution type or solution concentration to be administered; wherein the solution container or solution container's shipping box, shipping container, connector, or tip protector contains the same color or pattern as that shown on the user interface's icon; wherein a unique color or pattern is assigned to each solution type or solution concentration.

The pinch valves may be driven by a continuous nominal DC voltage level, AND are driven by higher than nominal DC voltage which is modulated by PWM to less than or equal to the nominal DC voltage after an initial short spike at or close to the higher DC voltage, wherein the valves' jaws are able to be opened after this spike phase even when no tubing is installed in the valves.

A 12 VDC battery can be used to power the pinch valves during AC power outage conditions, AND wherein a buck-boost circuit is used to boost the 12 VDC power from the battery to 18 VDC to drive the pinch valves during AC power outage conditions, wherein the cycler may continue delivering fluid to or from the patient during AC power outage conditions.

The heater plate can be driven by AC power when AC power is available, wherein a 12 VDC battery is used to power the heater element during AC power outage conditions, wherein a boost circuit is used to boost the 12 VDC power from the battery to a substantially higher voltage (greater than or equal to 24 VDC) to drive the heater element during AC power outage conditions, AND wherein the cycler may continue heating fluid in the heated dialysate bag and delivering fluid to or from the patient during AC power outage conditions.

The first pinch valve can be in its higher average voltage "spike" phase, the microcontroller prevents a second closed pinch valve from being commanded to open until after the first pinch valve's spiking phase is complete and it has transitioned to the lower "holding" average voltage.

An automated peritoneal dialysis (APD) system can communicate with the user's cellular phone via wireless or wired technology AND wherein the user's phone communicates with a server which communicates with the patient's clinic to transmit therapy results to the clinic or transmit one or more new prescriptions to the APD device.

An object of the system is to provide an improved automated peritoneal dialysis device.

Another object of the system is to provide a gravity-based APD device, which offers cost benefits, less pain during inflow and/or outflow, and which operates at lower absolute value pressures (both inflow and outflow), which has potential to reduce the likelihood of peritoneal membrane damage and associated hernias, pleural effusions, and other peritoneal dialysate fluid leakage outside the peritoneal cavity.

Another object of this system is to provide an APD disposable tubing set without a cassette, which offers cost benefits over traditional cassette-based tubing sets.

Another object of this system is to reduce the likelihood of peritonitis, specifically due to touch contamination.

Another object of this system is to prevent users from loading the disposable tubing set in an improper orientation.

Another advantage of this system is to provide an APD device which takes up a small floor footprint within the patient's home.

Another advantage of this system is to provide an APD device which is portable, both within the home and outside the home for travel.

Another advantage of this system is to provide an APD device which minimizes the likelihood of unintended Increased Intraperitoneal Volume (IIPV) and free flow.

Another advantage of this system is to reduce the noise during APD therapy.

Another object of the system is to provide an improved APD device which is of a design which assists the user in lifting dialysate bags to a higher height.

Another advantage to the system is it may use the patient's body weight to push or pull downward on one mechanism component in order to raise the height of the dialysate bags.

Another advantage of the system is its user interface helps users connect the disposables, including connecting the proper dialysate solution concentration that is needed for a given therapy on a given day.

Another advantage of the system is it provides better flow rates during filling and draining than other APD devices, which can reduce dwell time and thus total therapy time required to achieve desired efficacy outcomes.

Another advantage of the system is it can continue delivering APD therapy when AC power is unavailable.

Another advantage of the system is it can fully open pinch valves with or without a tubing set installed within the valves' jaws.

Another advantage of the system is it can operate on a single, relatively inexpensive 12 VDC battery.

Another advantage of the system is it is easier to drain the contents of the reusable drain container with the use of a valved spigot, vent, and/or handle.

Another advantage of the system is the drain container is reusable, thus reducing the cost and environmental impact vs. disposable drain containers.

Another object of the system is to reduce the maximum drain container weight a user is required lift to transport and empty the contents of a reusable drain container.

Another advantage of the system is it is easy to program the therapy parameters using either the Total Therapy method or the Number of Cycles method, without having to choose which method to use.

Another advantage of the system is its user interface supports illiterate or low-literacy users via icons and pictorial guidance, in addition to text-based prompts.

An advantage to the system is it provides an APD device which uses certain off-the shelf components which may include a commercially available IV pole to reduce cost, improve portability, and facilitate modularity.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 20 illustrates an example therapy programming screen with color coding to match the dialysate bags and/or dialysate boxes.

FIG. 21 illustrates an example therapy confirmation screen with color coding to match the dialysate bags and/or dialysate boxes.

It should be noted that various changes and modifications to the presently preferred embodiments described herein will be apparent to those skilled in the art. Such changes and modifications may be made without departing from the spirit and scope of the present system and without diminishing its attendant advantages.

DETAILED DESCRIPTION

Figure 1:
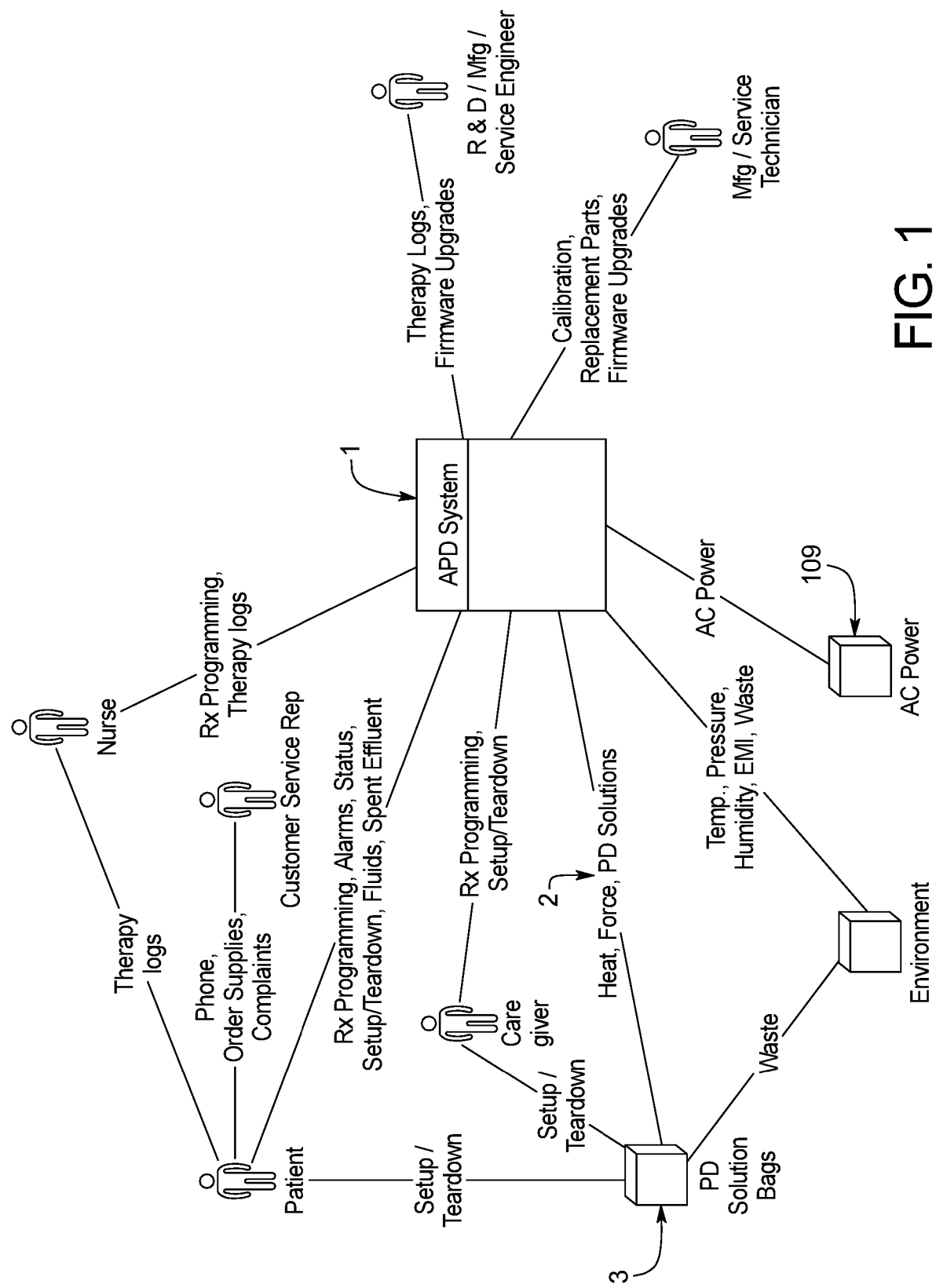
FIG. 1 illustrates a context diagram of an APD system and its external interfaces.
Figure 2:
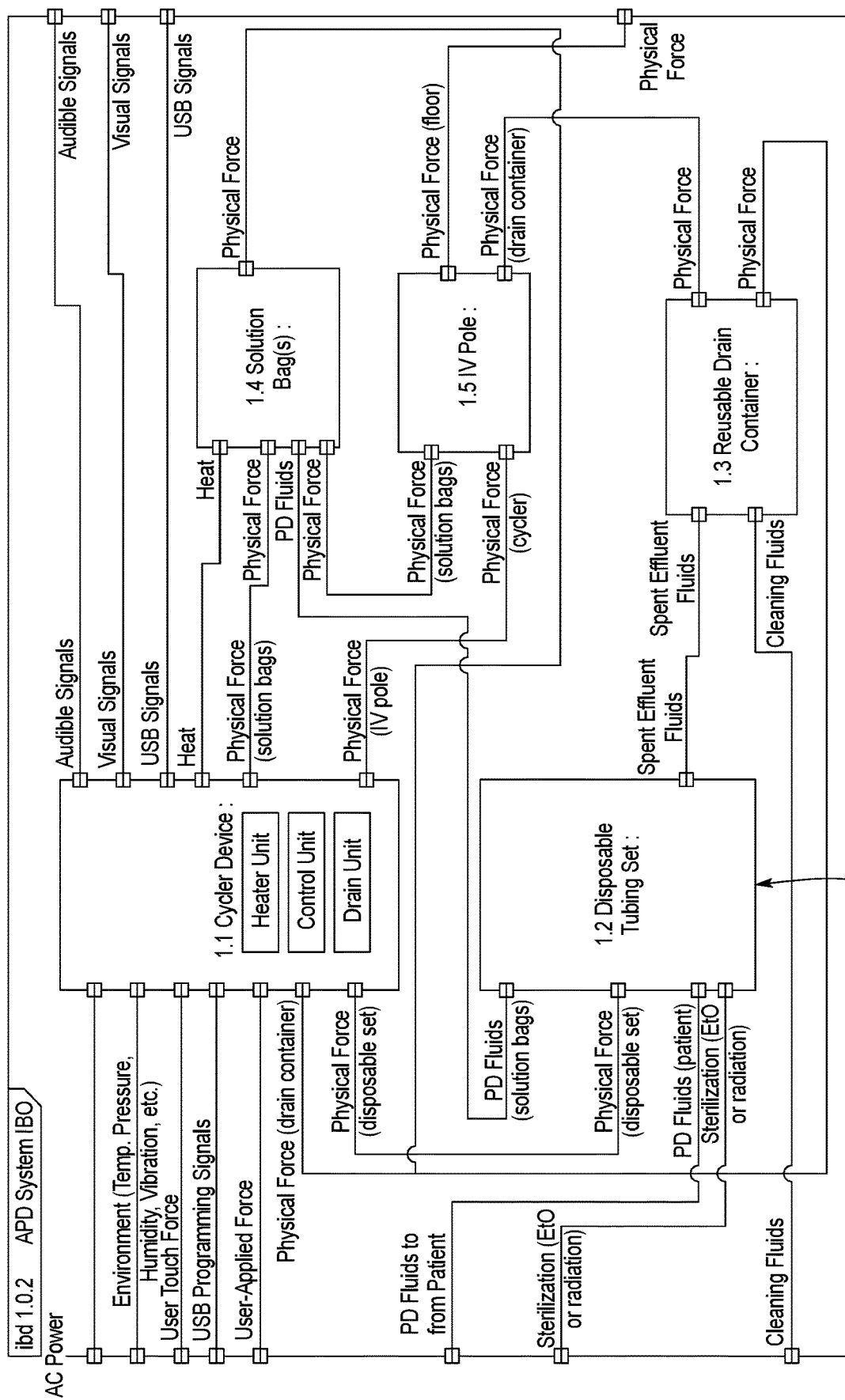
FIG. 2 illustrates an internal block diagram of the major components that make up the APD system.

The present disclosure provides an APD cycler system 1 that delivers APD therapy via gravity dialysate fluid 2 flow through a single use, non-reusable disposable tubing set 7 placed into the cycler's electronically-controlled pinch valves 23. External system interfaces are shown in FIG. 1. An internal block diagram of the major APD Cycler system components is shown in FIG. 2.

Figure 3:
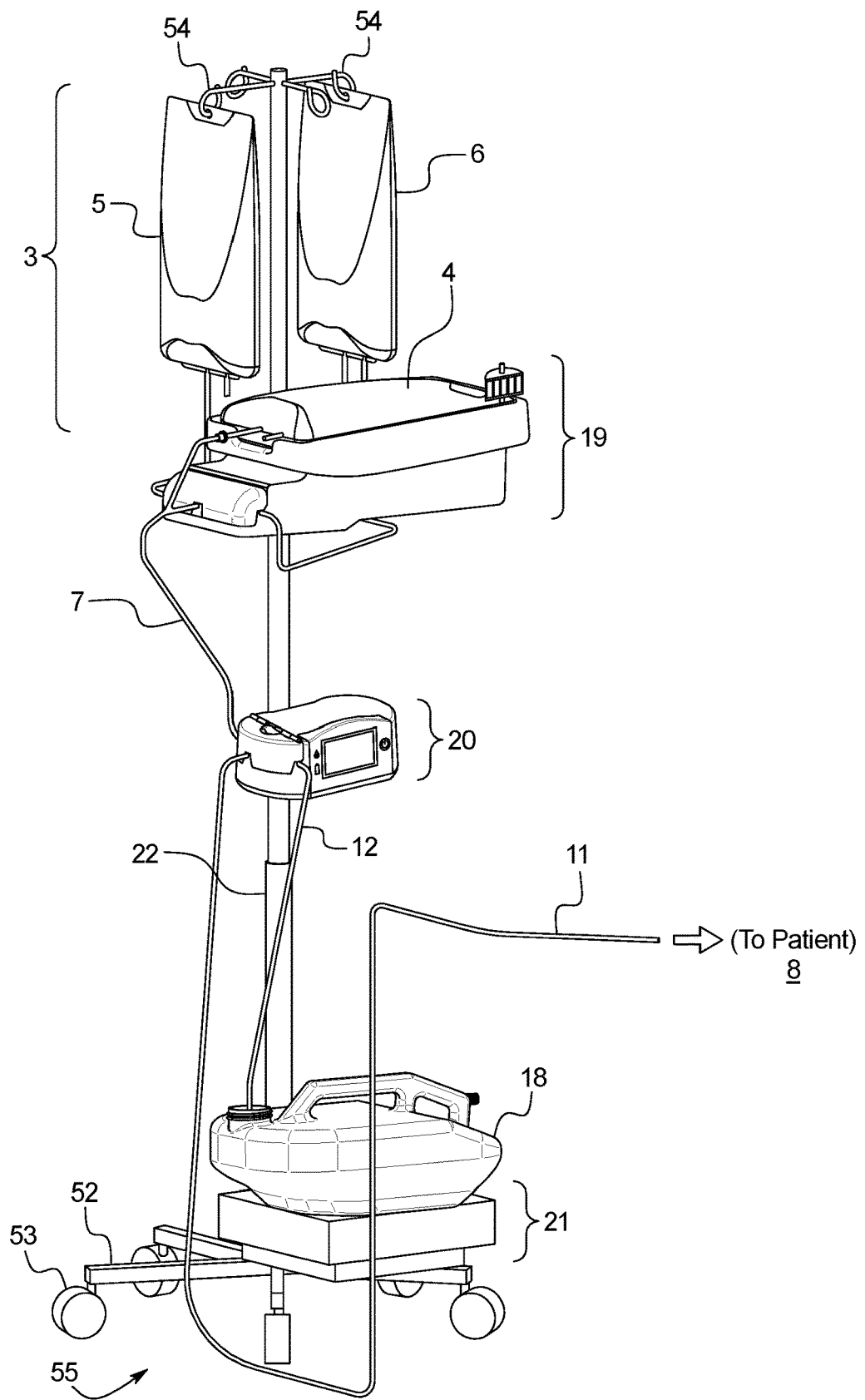
FIG. 3 illustrates the APD Pro system using an IV pole as the proposed pole and supports up to 3 total dialysate bags (Heater Bag, Supply Bag, and Last Fill Bag).

The system can also include a disposable tubing set 7, that interfaces with the cycler's hardware pinch valves 23, the patient 8, the drain container 18, and peritoneal dialysate bags 3. This tubing set connects up to 2 off-the shelf dialysate bags (Standard) or up to 3 dialysate bags (Pro) as shown in FIG. 3. The disposable set's patient line 11 connects to the patient's 8 transfer set 10, which in turn is connected to the patient's surgically implanted peritoneal catheter 9. The disposable set's drain line 12 allows fluid to drain into the reusable drain container 18 whose capacity is either greater than or equal to 15,000 mL or greater than or equal to 18,000 mL. The patient line is fitted with a disposable pinch clamp 16. The patient uses reusable removable plastic pinch clamps to shut off flow to/from the heater line 13, supply line 14, last fill line 15 (Pro only), and drain line 12. The system supports up to 15,000 mL (or 18,000 mL Pro model) of fresh dialysate per therapy, and up to 15,000 mL (or 18,000 mL) of drained dialysate in the Reusable Drain Container 18 before the drain container must be emptied.

Figure 15:
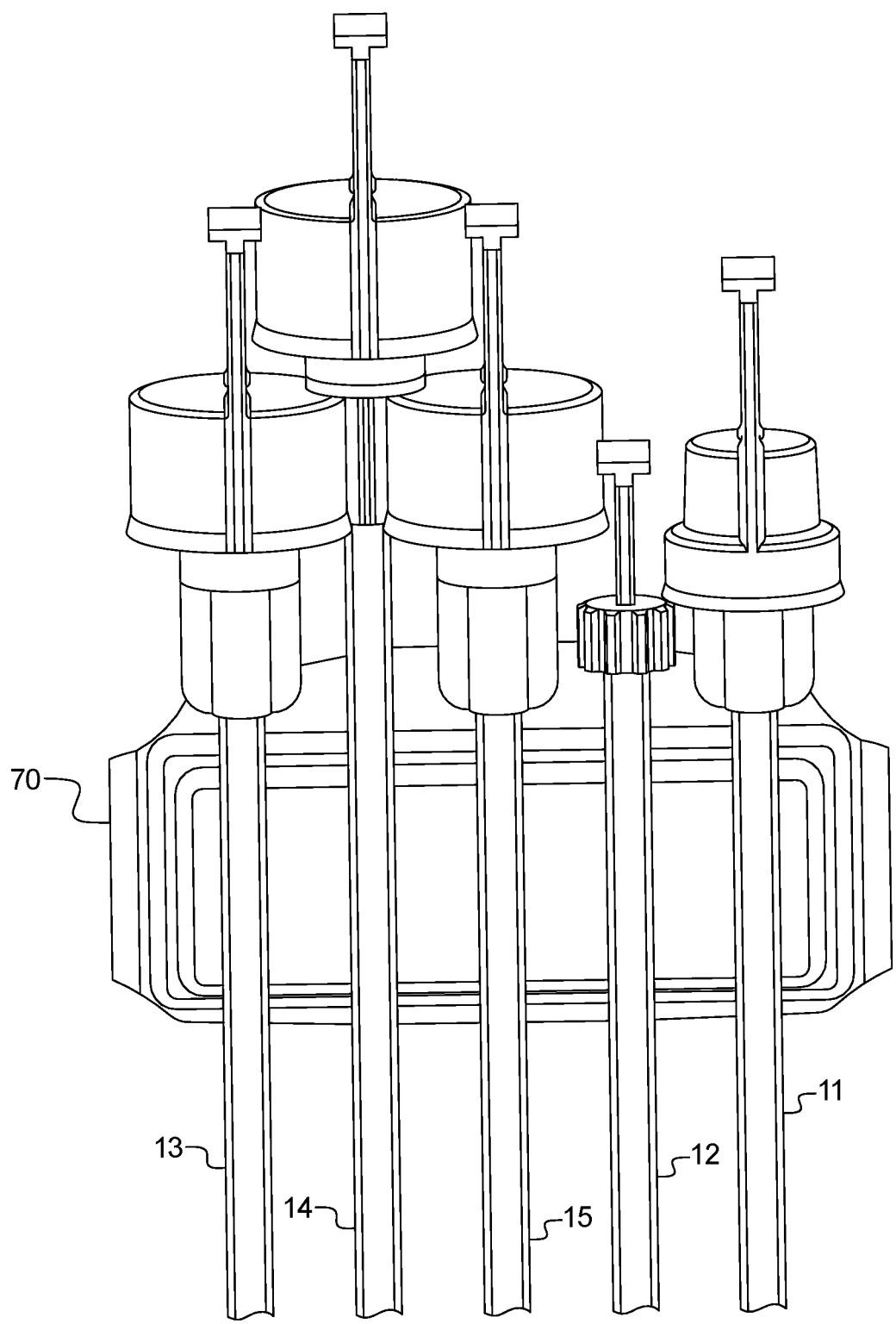
FIG. 15 illustrates a disposable tubing set tubing organizer with corresponding tubes installed.

The system can include hardware enclosures including, but not limited to, a Heater Unit 19 (FIG. 15 and FIG. 9), a Control Unit 20 (FIG. 11), and a Drain Unit 21. These enclosures are mounted on a pole 22. Each of these components is briefly described below.

The system can include the Heater Unit 19 mounted via the Pole 22 such that the Heater Unit remains above the height of the patient's peritoneal catheter, assuming the patient is sleeping in a bed or sitting in a chair during therapy, either of which sits approximately 20"-36" off the ground. Such configuration provides a solution as a gravity APD device heater unit.

Figure 14:
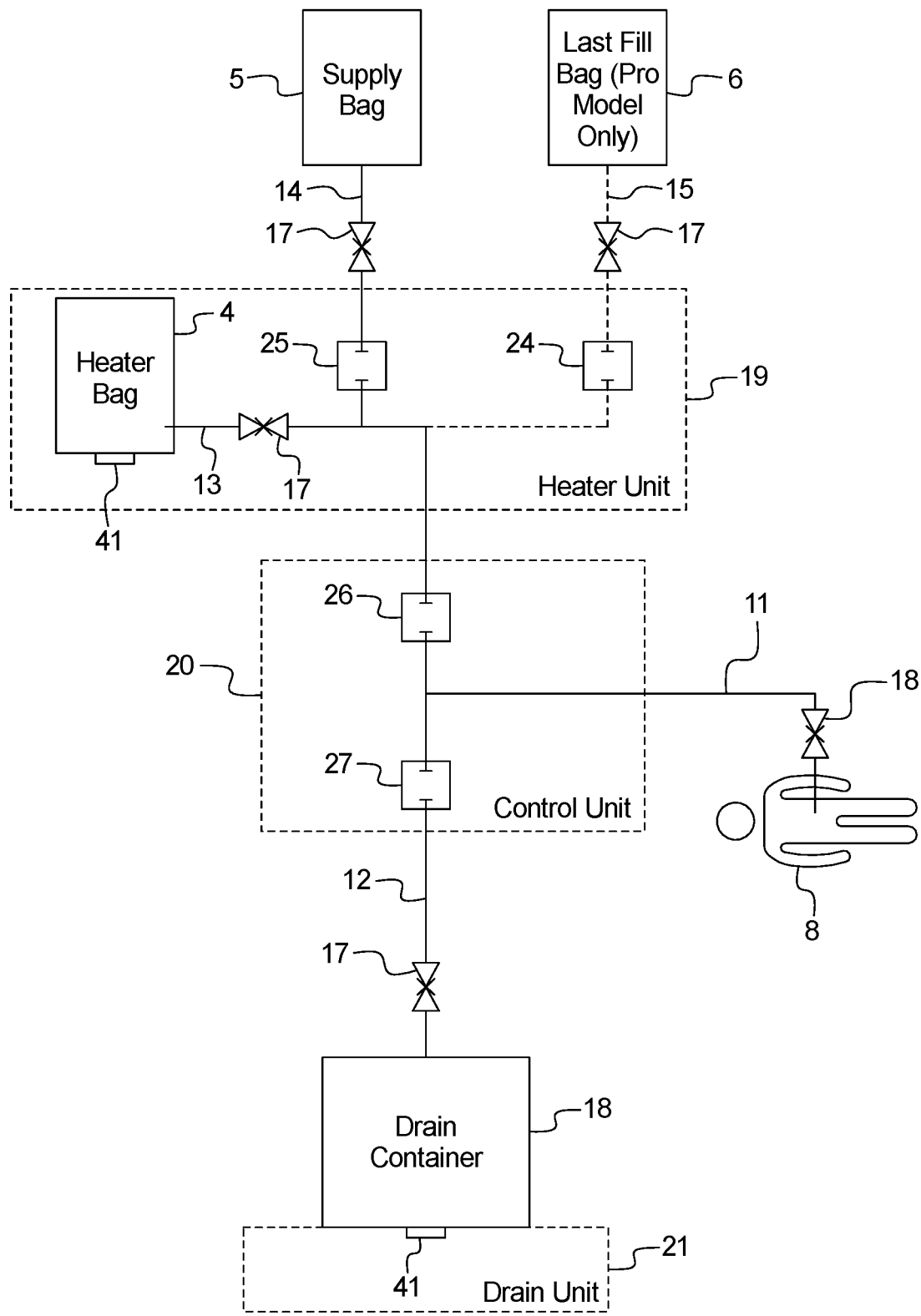
FIG. 14 illustrates a fluid flow schematic for the APD system.

The system can use of either one (Standard) or two (Pro) DC-powered, solenoid-driven, normally closed pinch valves 23 to control fluid delivered via the disposable tubing set to replenish either from the Supply Bag 5 to the Heater bag 4 via the Supply Replenish pinch valve 25, or the $2^{nd}$ optional Last Fill Replenish pinch valve 24 controls fluid delivered from the Last Fill Bag 6 to the Heater Bag 4 as shown in FIG. 3. A fluid flow schematic is shown in FIG. 14.

The system can include a plastic door 28 that covers the pinch valve(s) 23 for noise reduction and to prevent the tubing set from becoming dislodged.

Figure 9:
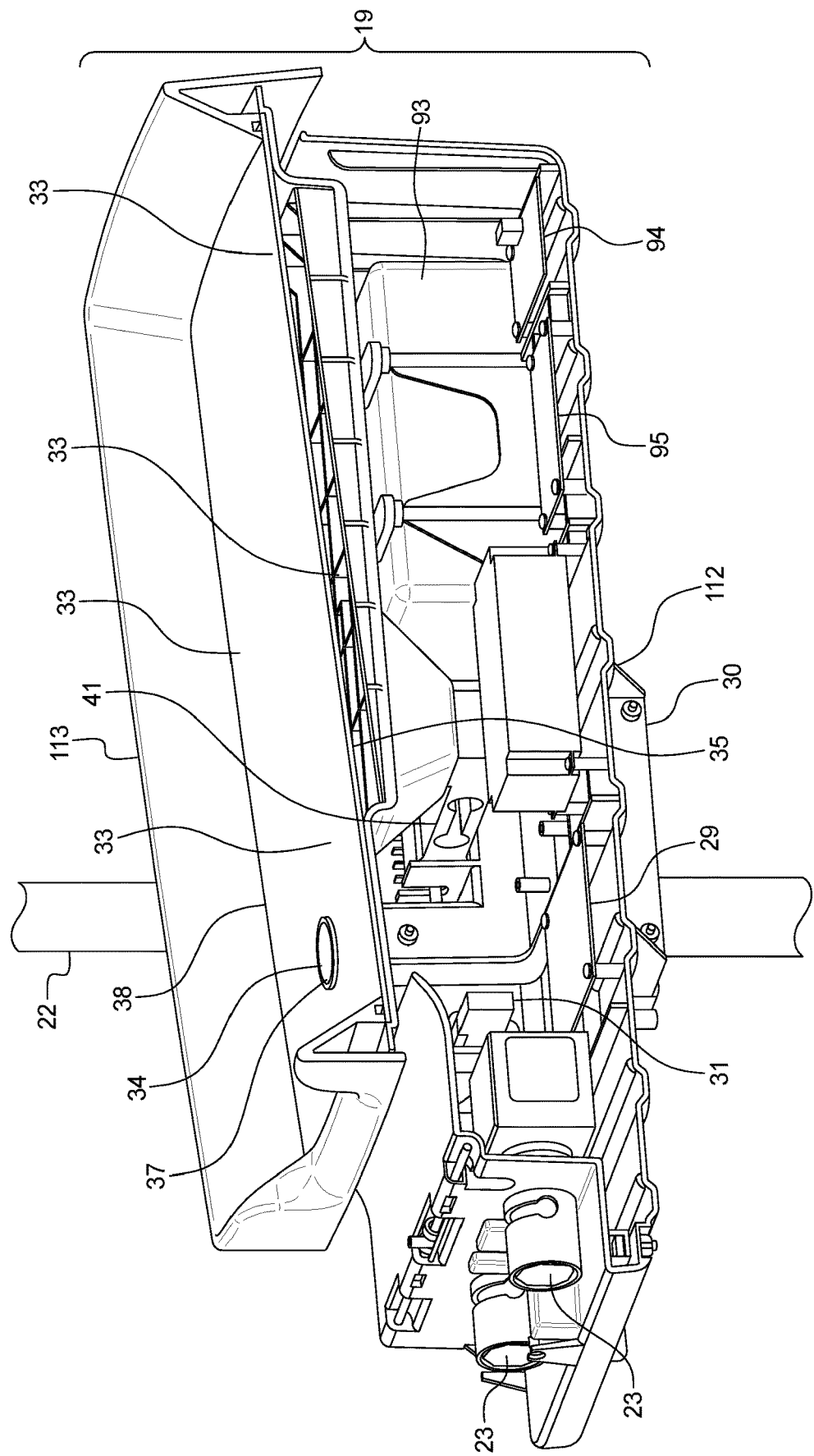
FIG. 9 illustrates a cross section of the Heater Unit.

An AC power routing and heater control circuit board 29 can reside within the Heater Unit 19, along with a DC power supply 30, 12 VDC battery 93, battery control circuitry 94, power management buck boost circuitry 95, and a 2-prong AC power entry module 31, with associated power cord (rated for electrical safety Class II per IEC 60601-1:2005+A1:2012) as shown in FIG. 9.

Figure 10:
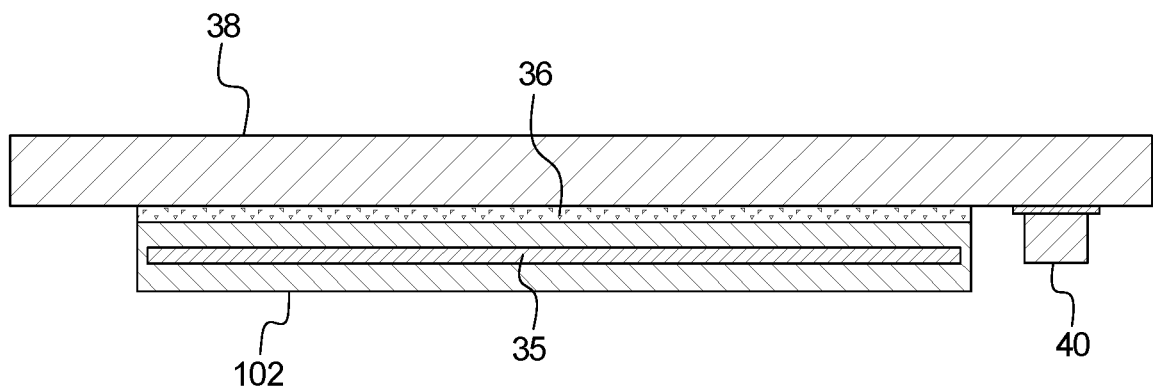
FIG. 10 illustrates a cross section of the Heater Plate, with corresponding electrical isolation materials.

The Heater Unit 19 can contain an elastomeric, foil-etched AC-powered heater element 35 integrated into a flexible silicone rubber casing 102 as shown in FIG. 10. The heater element can be bonded to a polyamide film 36 used a $2^{nd}$ means of electrical isolation, which is then bonded to the under-side of an aluminum heater plate 38 to heat fluid in the Heater Bag 4 containing up to 6,000 mL of dialysate solution 2. Four plate temperature sensors 33, such as thermistors in an example, measure heater surface temperature adjacent to four sides of the heater element 35 (forward, back, left, and right sides), although another embodiment could utilize only three (forward, back, and right sides), assuming the left and right sides are approximately equal temperatures. One or more additional bag temperature sensors 34, such as two thermistors in a preferred embodiment, measure Heater Bag temperature, bonded to the underside of a metal cap 37 protruding from the heater plate 38 surface. A control unit 20 uses the thermistors as inputs to turn on or off the heater element 35 so as to ensure that the maximum heater plate surface temperature does not exceed safe limits to prevent burns. A bimetal thermal cutoff AC power switch 40 is bonded to the underside of the heater plate 38, which cuts off power to the heater element 35 in the event of excessive temperature. This serves as a safety mechanism for runaway heater protection to prevent fires and burns.

The system can use of one or more load cells 41 envisioned beneath the heater plate to weigh fluid in the Heater Bag 4, which allows the device to measure volume filled into the patient, where volume is calculated by taking into account the density of fluid delivered (V=mass/density). In one embodiment, a single highly accurate load cell sits between the heater plate subassembly and the base of the top module enclosure. In another embodiment, up to 4 highly accurate body load cells sit below the heater plate near each of the 4 corners.

Figure 11:
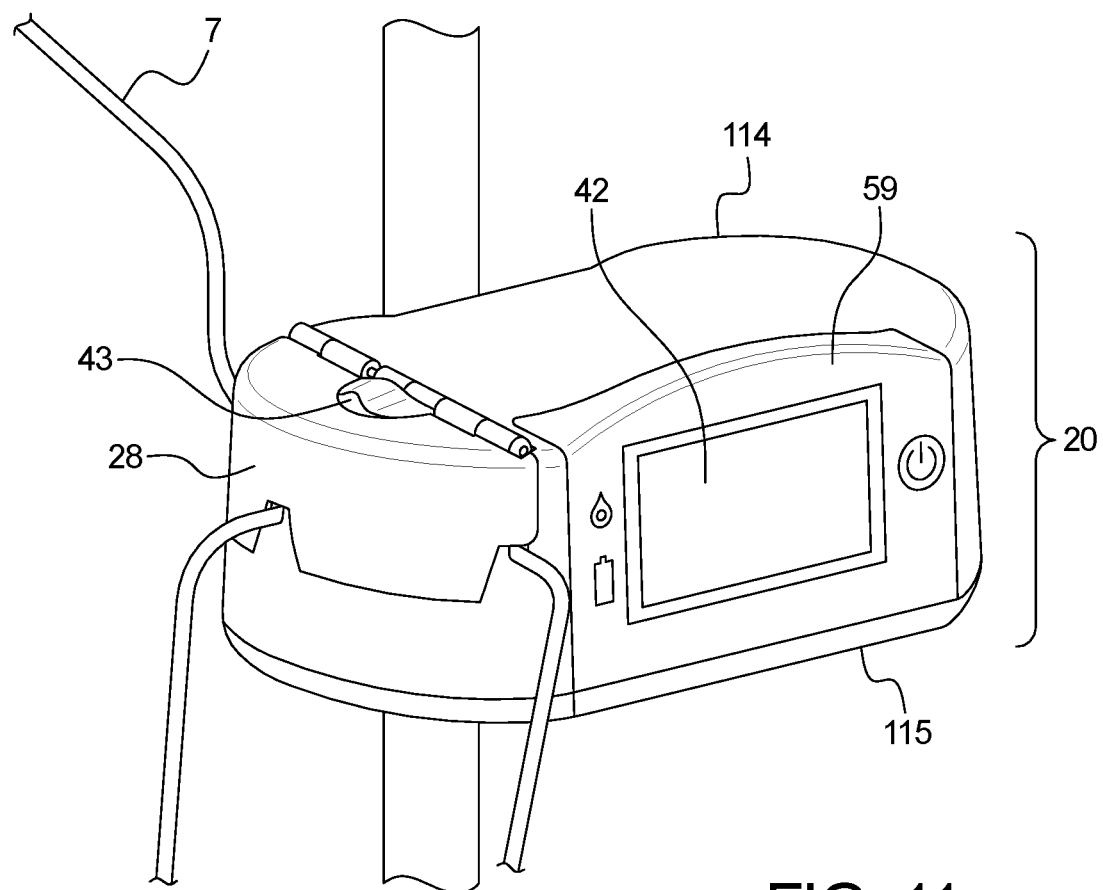
FIG. 11 illustrates the Control Unit mounted to the Pole.
Figure 12:
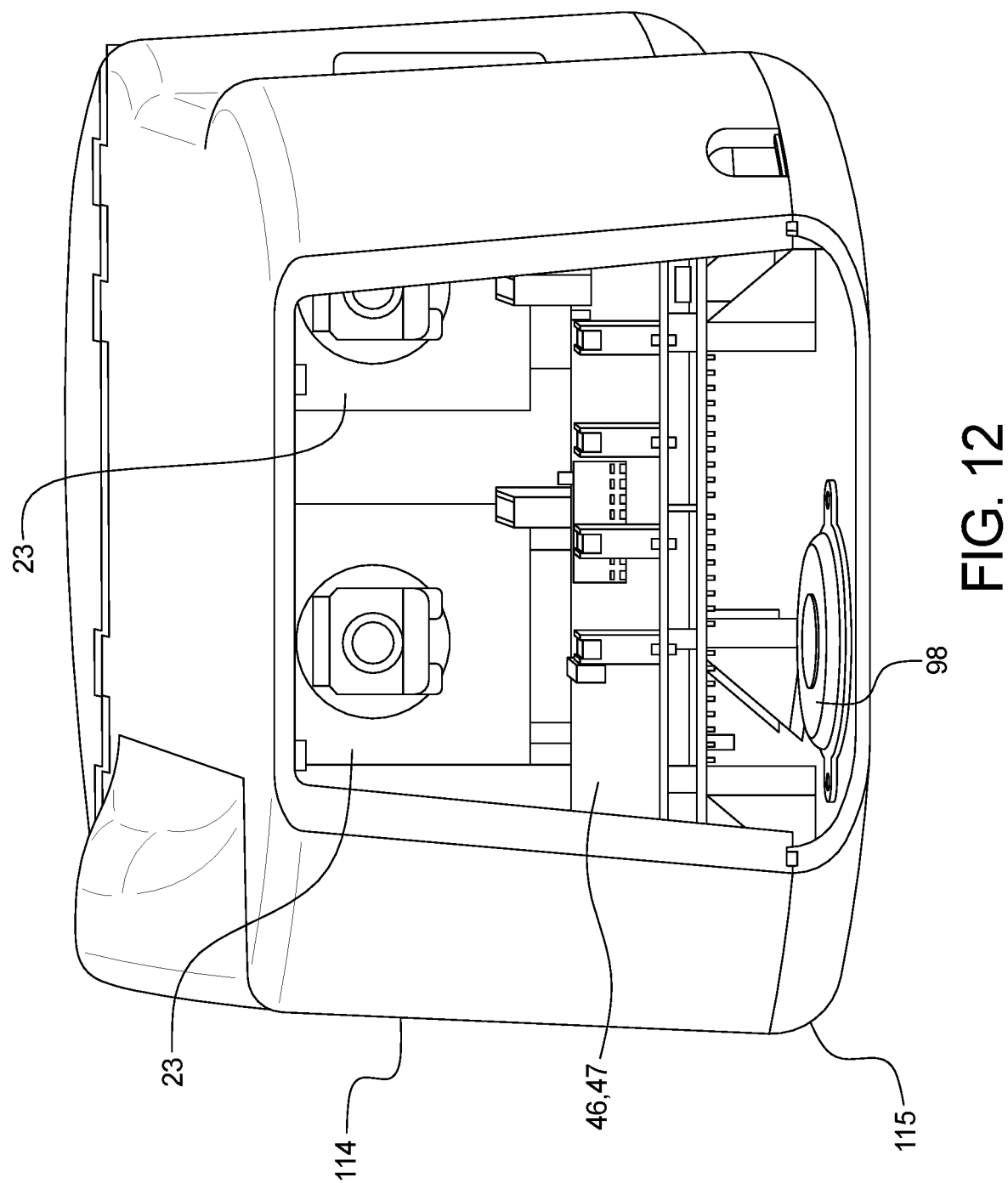
FIG. 12 illustrates a cross section of the Control Unit.

The Control Unit 20 can be mounted below the Heater Unit 19 and above the Drain Unit 21. The Control Unit 20 can contain a color touch screen user interface 42, two pinch valves 23 (one for filling 26, the other for draining 27 the patient), a door 28 covering the pinch valves, and a main control board 46 with a microcontroller 47 and associated memory for controlling system inputs and outputs, as shown in FIG. 11 and FIG. 12. A button panel 59, such as a membrane panel, is described in the User Interface section. The door can contain a latch 43 spring-loaded to the closed position via compression spring, and a hinge torsion spring to spring-load the door to the opened position. The compression spring ensures that the user must actively move the latch with a finger or thumb to the opened position so it does not inadvertently open during therapy and pose a tubing dislodgement risk and subsequent overfill/IIPV risk. The hinge torsion spring encourages the door to begin to spring open before the door latch moves back to the closed position.

A speaker 98 can be mounted to the inside bottom of the Control Unit provides audible alarm information in one embodiment and can additionally provide voice-guided instructions to the user in another embodiment. Slits are molded into the bottom of the Control Unit to enhance speaker output, while maintaining ingress protection from fluid spilled over the top of the Control Unit, such as in the event of a dialysate solution bag leak.

A USB memory stick with sufficient capacity to store at least 90 days of treatment information may be inserted into the Control Unit's USB port as an optional feature. The APD device may read and/or write prescription information from the USB stick for device programming and may record therapy results including programmed therapy and actual fill and drain volumes to the memory stick in less than 30 second intervals.

Data may be exchanged with the APD device via the USB port in one embodiment, or via other wired or wireless methods, including, but not limited to, serial such as RS-232, ethernet, Bluetooth, Wifi, or other wired or RF method. A service technician may upload new therapy firmware to the APD device via the USB port. This data may include therapy data, machine diagnostics, prescription information, and/or firmware updates to write to or read from the device.

An external wireless dongle may be connected to the USB or other wired port to provide wireless transmission capabilities to the APD device, which could enable remote therapy prescription changes and/or remote therapy results monitoring. The wireless dongle could communicate directly to the clinic via wifi or cellular modem technology. The system can include the use of wireless technology in our APD device that could be connected to the patient or user's phone which then connects to a server which the clinic's patient-monitoring software interfaces with, using the phone's wireless data transmission capabilities via a phone application. A cable can connect the Heater Unit to the Control Unit, with another cable connecting the Drain Unit to the Control Unit.

The Drain Unit 21 mounted below the Control Unit as shown in FIG. 3. The Drain Unit, measures fluid volume drained from the patient. The reusable drain container 18 sits atop the Drain Unit. One or more load cells 41 are envisioned beneath the drain unit's top surface to weigh fluid in the reusable drain container 18, which allows the device to measure volume drained from the patient, where volume is calculated by taking into account the density of fluid drained (V=mass/density). In one embodiment, a single highly accurate load cell sits between the drain unit's sides support cover and the base of the drain unit's enclosure. In another embodiment, up to 4 highly accurate body load cells sit below the heater plate near each of the 4 corners. In an example, the bottom of the load cell(s) are mounted directly to the alternate metal pole 22 structure to provide additional stability and enhance measurement accuracy versus mounting them onto a plastic base.

In an example, the Pole 22 is a conventional IV pole with a weighted base to provide additional stability. The Heater Unit, Control Unit, and Drain Unit mount to the pole via pole clamps 51. In this embodiment, the IV pole has 5 or 6 legs 52 on casters 53 on its base 55 and a minimum of 2 bag hooks 54 at the top of the pole. The legs 52 and/or base 55 must weigh at least 8.2 kg to provide stability to counter the weight of up to three dialysate bags 3 at up to 6 kg apiece, plus the three APD Cycler enclosure modules (Heater Unit 19, Control Unit 20, and Drain Unit 21) which mount to the pole 22, weighing approximately 6.8 kg, 2.1 kg, and 3.5 kg, respectively. The pole diameter may range from 0.75" to 1.5". The pole must be capable of extending to a height which falls within the range of 60" to 75".

Figure 8:
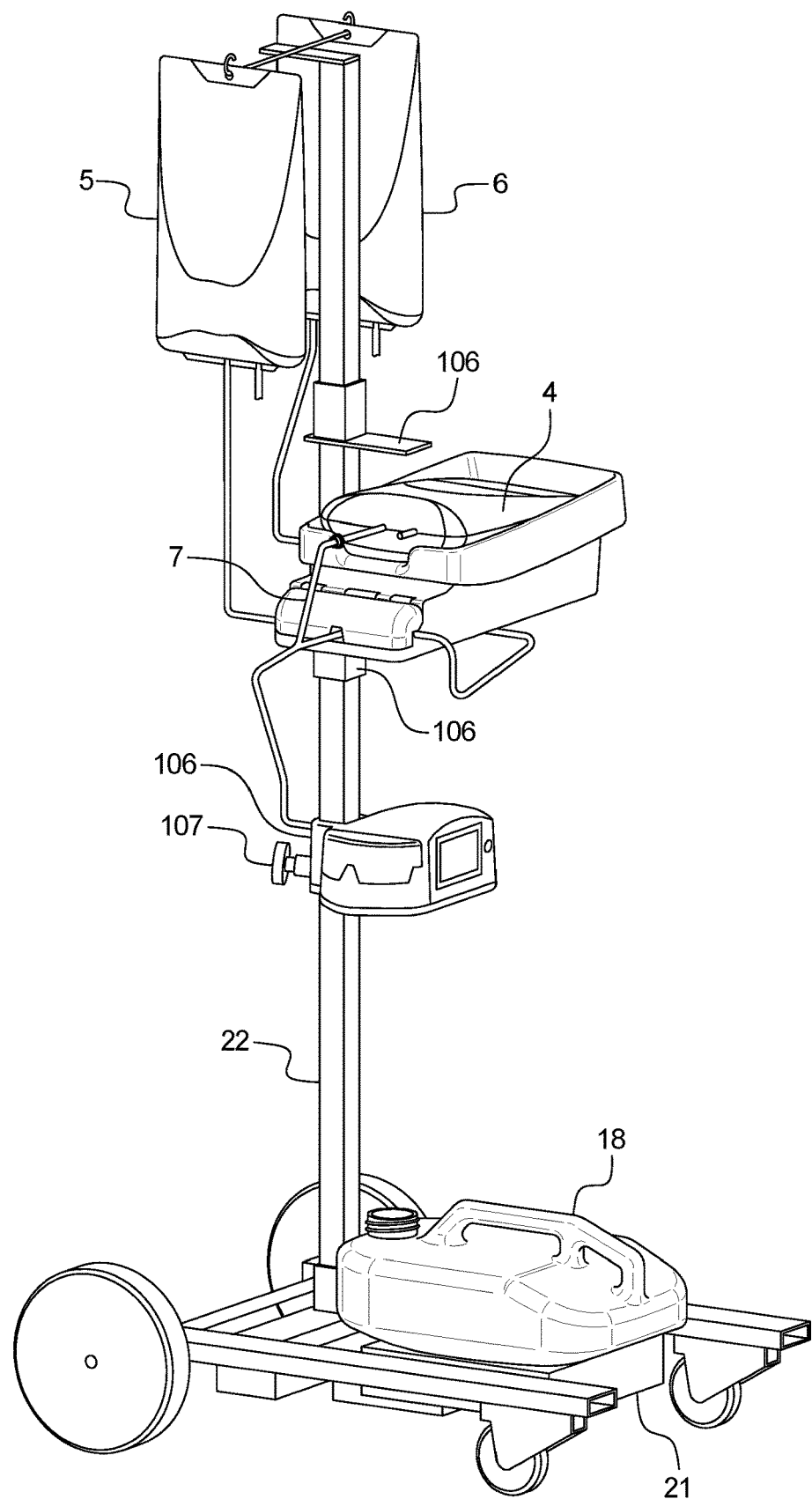
FIG. 8 illustrates an APD device using the alternate pole assembly, wherein the system includes the Heater Unit mounted to the pole, with heater bag, supply bag, and last fill bag mounted.

The Pole 22 can be integrated with the Drain Unit 21, as shown in FIG. 8. In this embodiment, there are a pair of larger, fixed-axis wheels on the left side of the base of the pole, coupled with a pair of smaller caster wheels 53 on the right side. The casters are rotatable in 360° and may be locking-type. The vertical structure consists of two or more concentric square tubes affixed to the base. The square tubes are perforated at regular intervals along the vertical axis to provide for variable height adjustment of the Heater Unit 19 and/or Control Unit 20. Adjustable Heater Unit heights allow shorter patients the ability to place the Heater Bag 4 onto the Heater Unit at a lower height, and allow patients needing greater Fill flow rates to achieve them by raising the Heater Unit. The Control Unit's adjustability allows patients to keep the Control Unit's display 42 and button panel 59 easily accessible for sleeping patients whose bed heights may differ from each other.

The pole, the Heater Unit, Control Unit, and Base/Drain Unit may be detached from the pole to facilitate portability for travel. The pole may collapse and/or disassemble into two or more shorter pole segments. It may also facilitate different APD device configurations by swapping out certain components or subsystems, while maintaining other components or subsystems, with each component or subsystem mounted to the IV pole. In one embodiment, this may include an optional push/pull handle to push or pull the entire pole and attached APD system within the home. In this manner, multiple region-specific APD device configurations may be envisioned. Additionally, one or more optional components or subsystems may be added to the APD device by clamping additional components or subsystems to the pole. This may include a component or subsystem 61 intended to assist in lifting dialysate bags to the proper height. The wheels and/or casters may be detachable from the base to further facilitate portability for travel.

Figure 13:
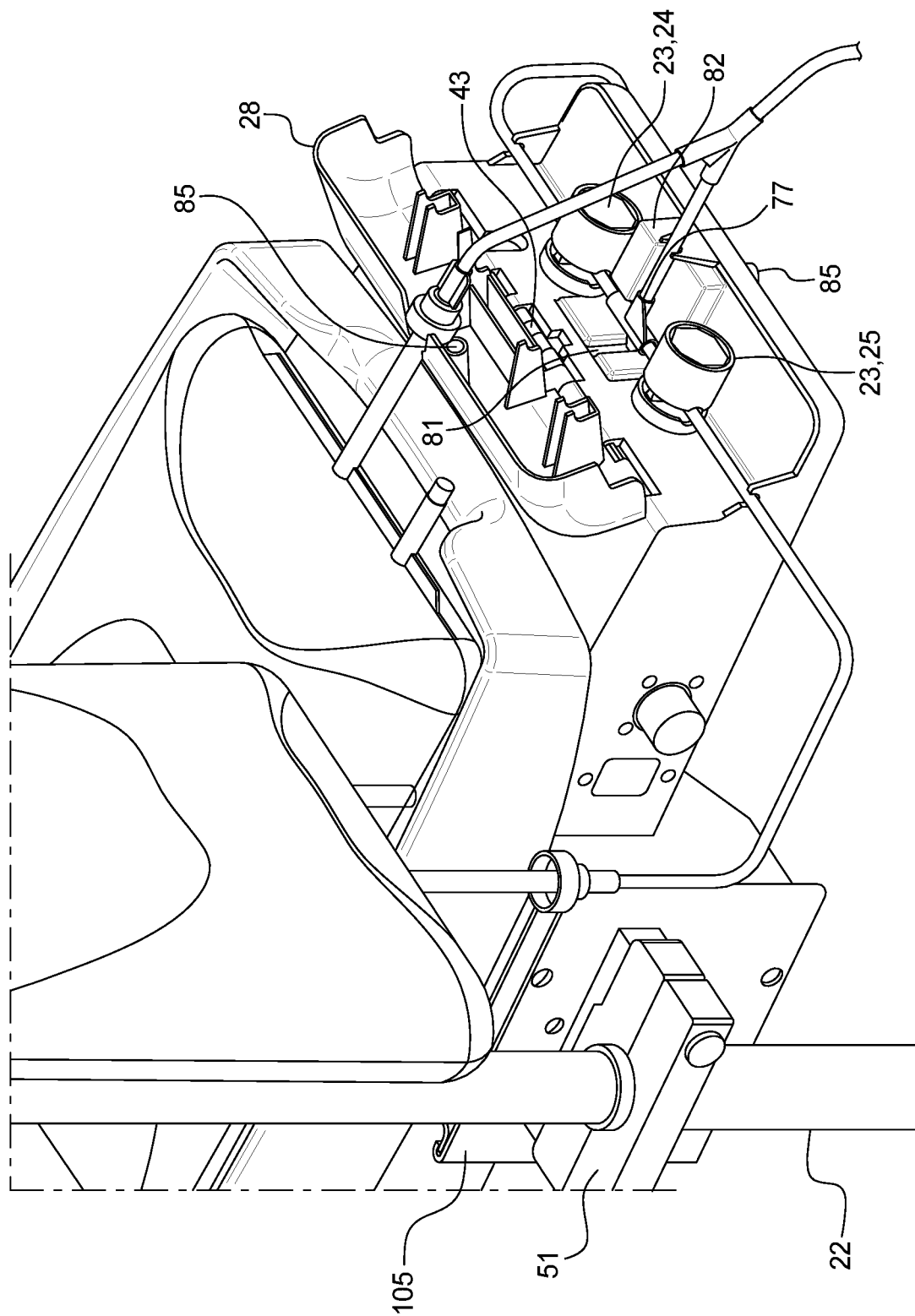
FIG. 13 illustrates the back view of the Heater Unit with a tube housing door, showing a proposed mounting bracket mechanism.

In one embodiment, the enclosure detachment mechanism is a pole clamp mounted on the back of one or more of the Heater Unit, Control Unit, and/or Drain Unit. In another embodiment, the male end of a big-screen television mount 105 (or similar apparatus) is attached to the back of the Heater Unit, with the female end attached to a pole clamp, which clamps to the pole as shown in FIG. 13. The Heater Unit is then attached to the pole by lifting the Heater Unit and sliding the male end of its TV mount down into the female end mounted on the pole. In another example, the detachment mechanism is a platform shelf bracket which attaches to the square tubing via a pin 107 placed into one of the perforated holes. The pin could be spring-loaded into the hole.

By utilizing a vertical structure, whereby the Heater Unit, Control Unit, and Drain Unit are affixed to the vertical pole, this offers advantages over traditional active pumping APD devices. Traditional APD devices typically have the Heater Bag mounted atop the device, with the Supply Bag(s) and Last Fill Bag situated next to the device. This requires the patient to have a large nightstand, table, or large cart to place all of these items, with a correspondingly large footprint on the patient's floor and little to no portability within the home. The vertical structure takes up less footprint on the floor. Additionally, with the inclusion of wheels in the pole's design, the system is more portable within the patient's home (or hospital) than traditional active pumping APD devices.

Figure 6:
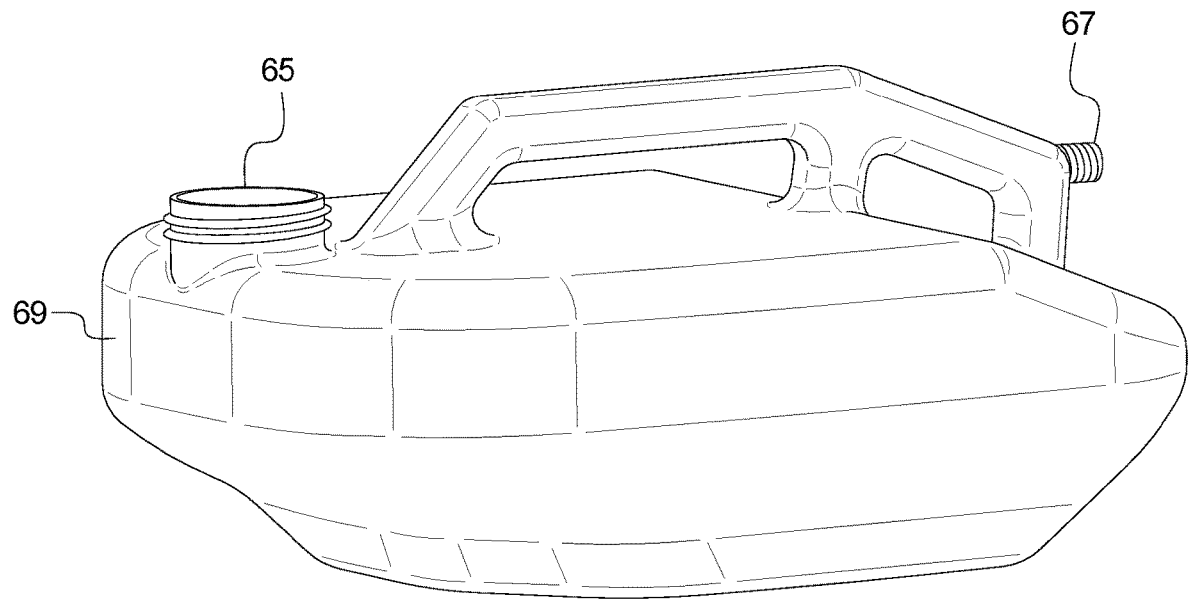
FIG. 6 illustrates a reusable drain container.

The system can include a reusable drain container 18, shown in FIG. 6, that sits atop the Drain Unit as shown in FIG. 3 to serve as a 15,000-20,000 mL reservoir for spent effluent drained from the patient. The drain container, in one embodiment, is transparent to allow the user to view the cloudiness of the spent effluent, which is a sign of potential peritonitis. A drain line clip integrates with the drain container to ensure an air gap is maintained between the disposable tubing set's drain line 12 and the maximum fluid level within the drain container. By offering a reusable drain container, this system saves cost over traditional APD devices which offer a single-use disposable drain container.

The reusable drain container contains a large spout 65 for pouring the contents into a floor drain, toilet, or tub. A removable spigot 66 with integrated valve may be placed over the spout via threaded connection via base 300, as shown in FIGS. 17A-D. This spigot allows the user to open the valve and leave the drain container draining (e.g. into a floor drain) while the user is able to walk away without continuously holding it and waiting for it to complete. A vent hole 67 and associated cap 68 is included on the opposite side from the spout to reduce sloshing while emptying the contents of the drain container. The drain container, in one embodiment, has a flat side 69 (FIG. 6) to allow the user to leave it on a toilet seat or floor drain in a tipped up configuration for the entire contents of its fluid to flow out the spout or spigot, again, allowing the user to walk away without holding it continuously to wait for it to complete.

Figure 7:
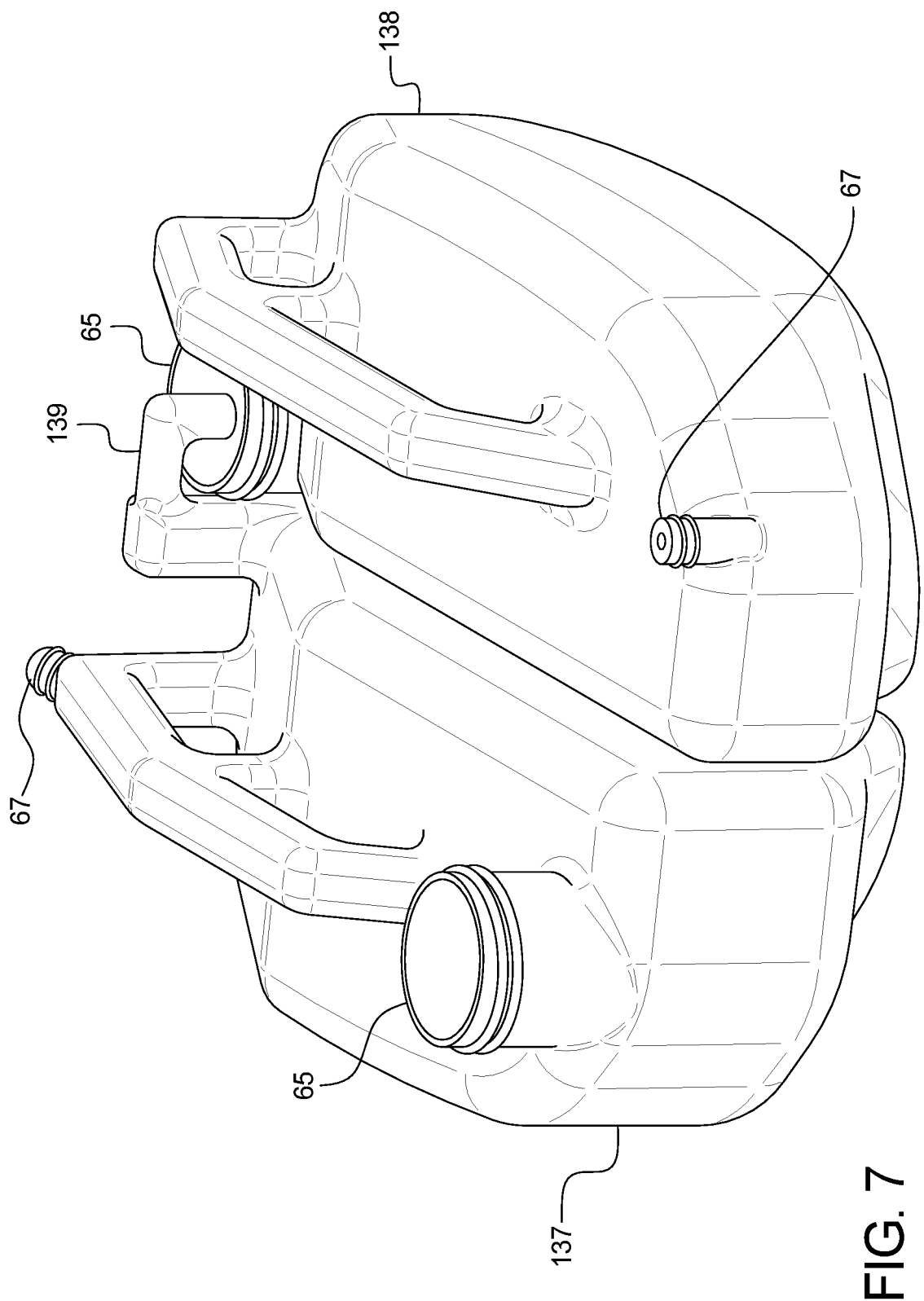
FIG. 7 illustrates an alternate reusable drain container configuration.

As shown in FIG. 7, the system can include an effluent drain receptacle that is split into two smaller reusable drain containers, a primary 137 and a secondary 138, each with a capacity of approximately half of the total system's drain capacity, which equates to approximately 7,500 to 10,000 mL each. The two drain containers can sit side-by-side on the drain unit 21. Alternatively, they could be arranged with the primary container in a toroidal shape, and the secondary container resting within the "donut hole" of the primary container, or vice versa. In either configuration, fluid from the disposable tubing set's drain line 12 flows into the primary container. The primary drain container contains an outflow spigot or port 139 which, when the container is full, begins delivering fluid to the secondary drain container as additional fluid is drained from the patient. The secondary container's spout 65 is positioned just below the primary container's spigot 139 such that it receives overflow fluid from the primary container. A cap may be placed over the containers' respective outflow spigot and/or the spout for transport and storage. Each of the primary and secondary containers also has a vent hole on the opposite side from the spout to prevent an internal vacuum while emptying the contents from the spout into a tub, toilet, or floor drain. This embodiment has the advantage of ensuring the user does not have to lift the entire weight of a single 15,000 to 20,000 mL drain container, but only has to lift approximately half that weight at any given time. Of course, any number of drain units can be used. For example, the system may have 3 or more drain containers with overflow fluid passing from one to the next to the next, rather than the two drain containers described herein.

Figure 4:
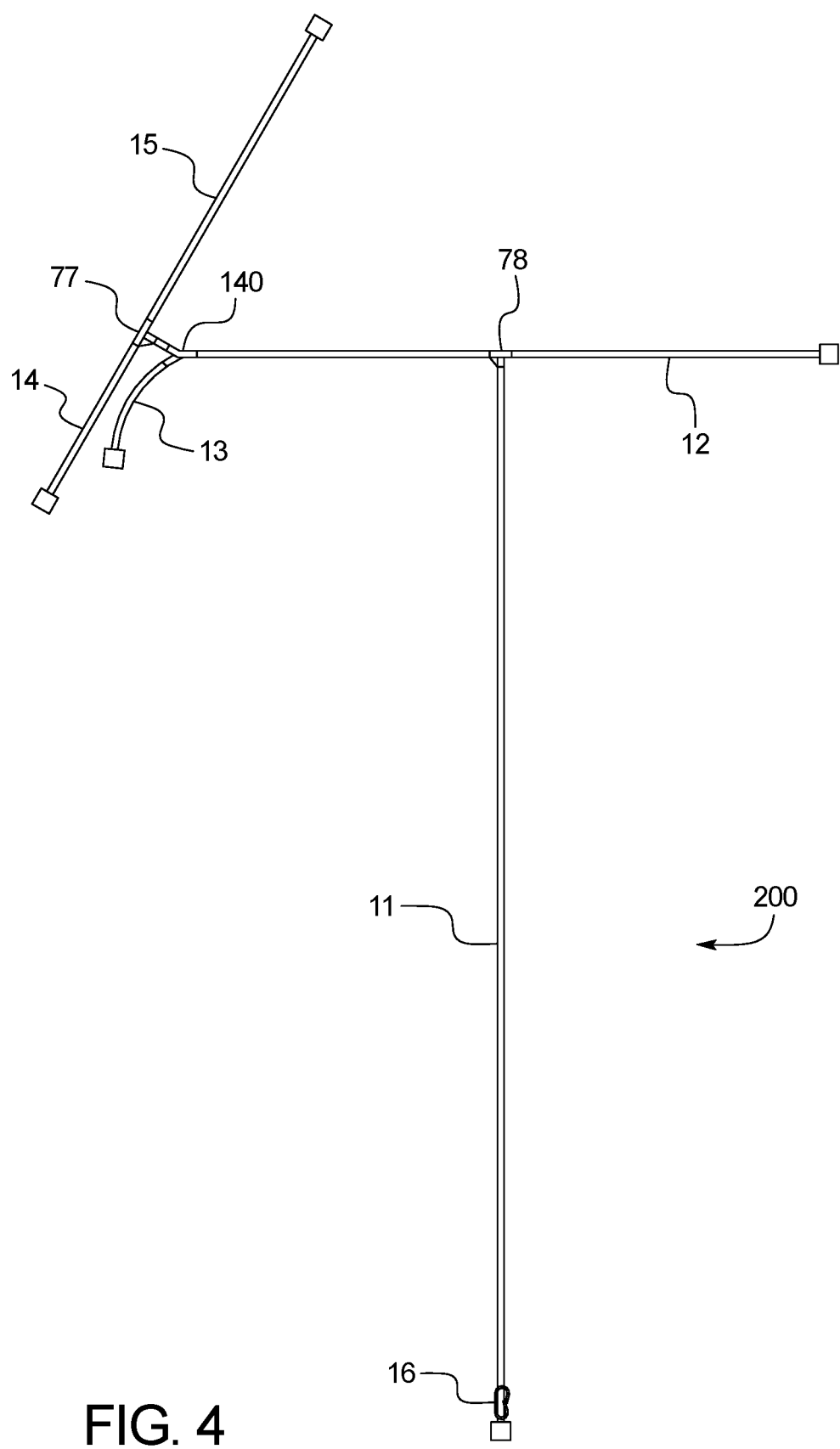
FIG. 4 illustrates the Pro model disposable tubing set with the extra tubing line and associated connector for connecting to a unique Last Fill Bag.
Figure 5:
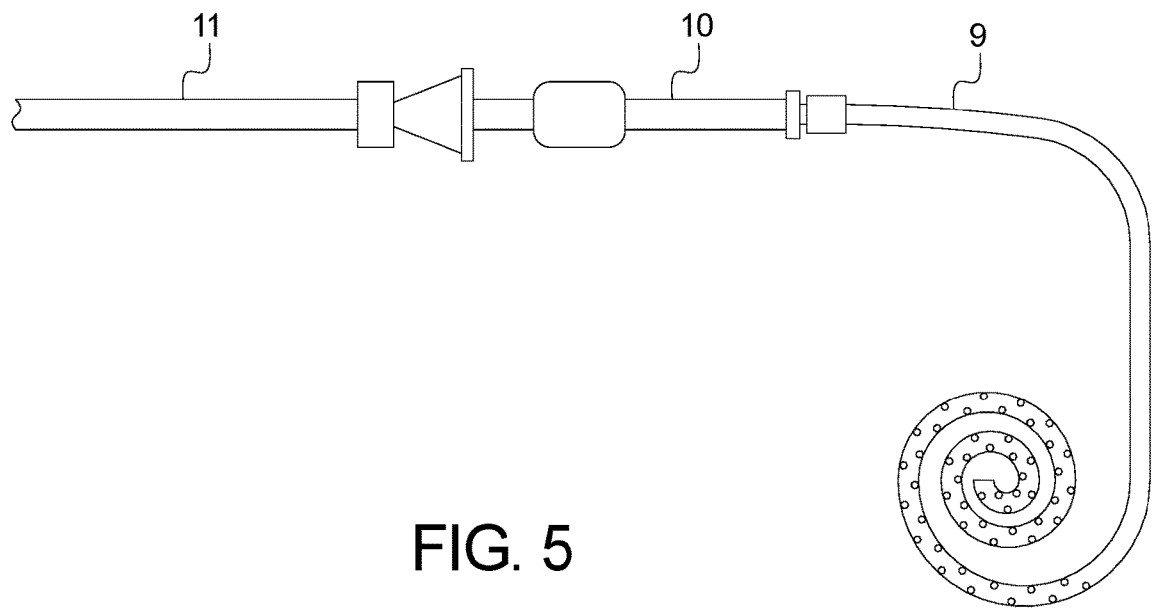
FIG. 5 illustrates how the proposed disposable tubing set (Standard or Pro) connects to a transfer set, which in turn connects to the patient's surgically implanted PD catheter.

The system can include a sterile, single-use disposable tubing set 200, as shown in FIG. 4, and its associated hardware interfaces. The proposed disposable set consists of medical-grade, biocompatible PVC tubing, a patient line tubing clamp, and molded plastic connectors with caps. Reusable clamps can be used for all tubing lines except the patient line, which has a disposable clamp integrated into the tubing set. Sets are available with multiple bag connector fitting types for interfacing to various off-the-shelf peritoneal dialysate bags. The internal contents of the tubing set are sterilized. Each tubing set can be packaged in a poly pouch, several of which are packaged together in a cardboard box for shipping and distribution.

The Standard model tubing set can contain a Heater Line 13 tube and associated connector for connecting to a Heater Bag. The tubing set can include a Supply Line 14 tube, associated connector for connecting to a Supply Bag, a Drain Line 12 tube for connecting to the Drain Container, and a Patient Line 11 tube and associated connector for connecting to the patient's catheter or catheter transfer set.

Figure 16:
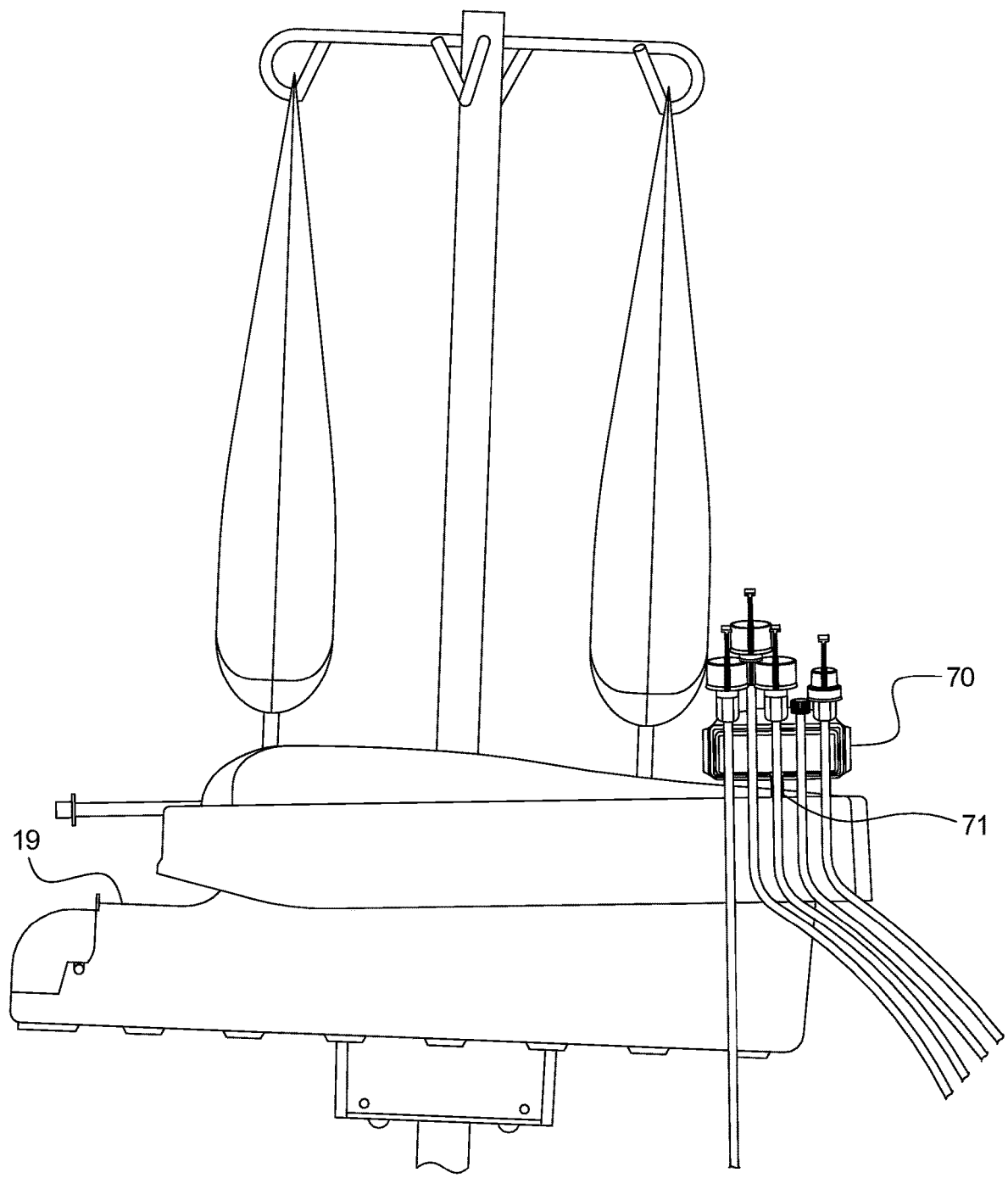
FIG. 16 illustrates the tubing organizer fully installed on the Heater Unit's organizer holder.
Figure 17A:
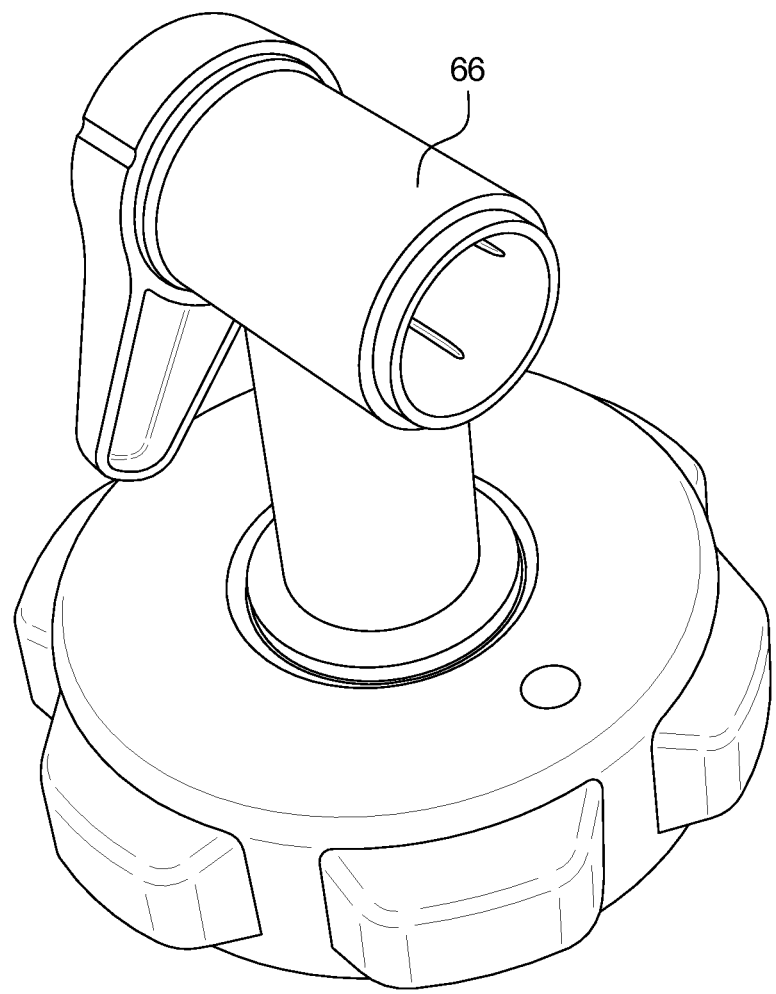
FIGS. 17A-17D illustrate the drain container spigot in both an assembled and disassembled fashion, as well as the drain container's vent cap.
Figure 17B:
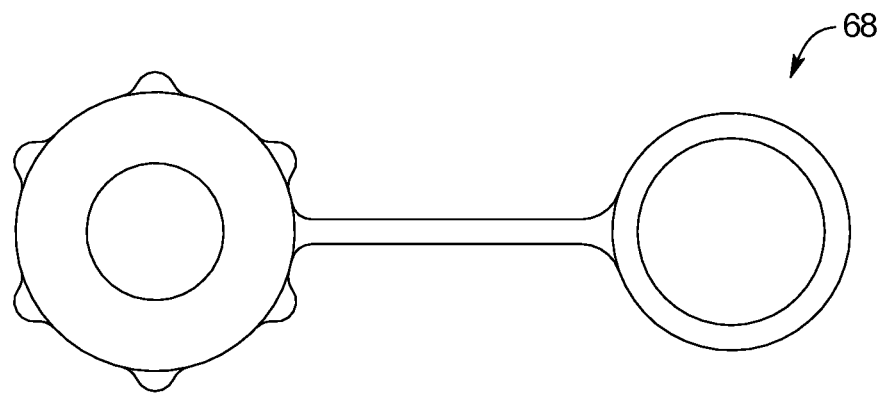
Figure 17C:
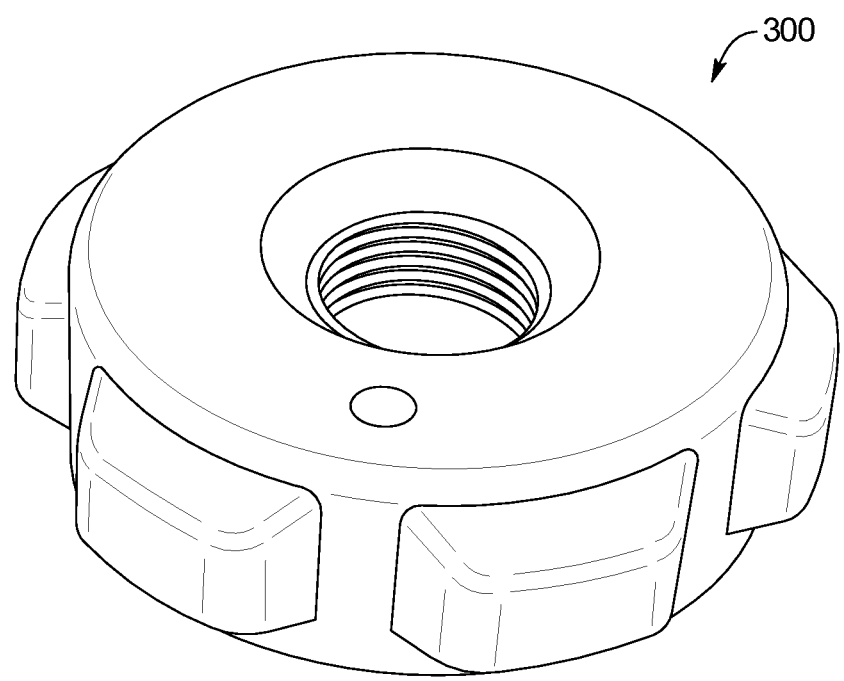
Figure 17D:
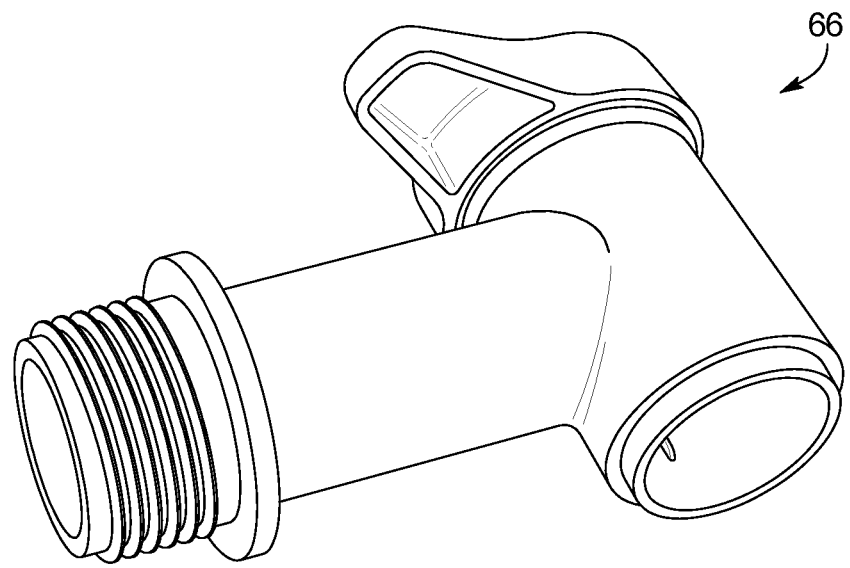

Unlike conventional APD tubing sets, the present system includes a tubing set which does not contain a cassette, since fluid flow is controlled via electronically controlled, solenoid-operated pinch valves and gravity provides the motive force for fluid delivery. All lines and/or connectors with exposed fluid paths are fitted with vented caps to maintain sterility and facilitate ethylene oxide sterilization. The solution lines, patient line, and drain line are placed in a tubing organizer 70 (FIG. 15), which are then mounted into an organizer holder 71 (FIG. 16) on the Heater Unit 19 during pre-therapy setup steps. The user then removes the lines from the organizer as instructed by the UI. The patient line 11, when inserted into the organizer and mounted onto the Heater Unit organizer holder, is placed such that the top of the Heater Bag 4 is approximately at the same height as, or just below, the top of the patient line 11 to facilitate gravity priming.

In an example, the disposable set for the Pro model is identical to that of the Standard except it contains one extra tubing line and associated connector to connect to the Last Fill solution bag 6. Both tubing set configurations may have one or more optional Y-fittings or manifolds to connect additional Supply Bags.

As shown in FIGS. 25A-25C and FIGS. 26-27, the system can include solution line connectors for connecting the Supply Bag, Heater Bag, and optional Last Fill Bag, which are designed to reduce the likelihood of peritonitis due to touch contamination. In one embodiment, a female Luer fitting 72 can mate to the shrouded male Luer fitting 75 affixed to commercially available APD bags. The female Luer fitting 72 contains a shroud 73 which extends above the surface of the Luer fitting's fluid path 74 to reduce the likelihood of touch contamination. The shroud 73 is also designed to fit around the shroud of the dialysate bags' male Luer 75, as well as to fit around the circular disc 76 used as a finger-hold in certain commercially available dialysate bags' male Luer fittings. In an example, the shroud 73 could surround a non-shrouded Luer female fitting or a non-Luer fluid fitting, provided that it still extends above the surface of the fitting's fluid path and the shroud fits around the corresponding mated solution line fluid fitting, with genders swapped as needed.

The tubing set contains a custom fitting 77 (e.g., Fitting #1) at the 3-way junction between the Supply Line 14, optional Last Fill Line 15, and Heater Line (via tubing headed toward the Control Unit in the direction toward the patient line, to which the Heater Line is connected via a wye fitting described hereafter). The Fitting #1 can be installed into the Heater Unit. Additionally, another similar custom fitting 78 (Fitting #2) exists at the 3-way junction between the line coming from the Heater Bag, the Patient Line 11, and the Drain Line 12, and is installed into the Control Unit. These custom Fittings #1 or #2 could be in the shape of a tee (3-way).

An additional wye fitting 140 can connect the Heater Line 13 to the tubing headed toward the Control Unit, with the third leg of the wye connecting to a short tube whose opposite end connects to Fitting #1. This allows either the Supply Bag or Last Fill Bag to replenish the Heater Bag by opening either the Supply Valve or Last Fill Valve.

Figure 28:
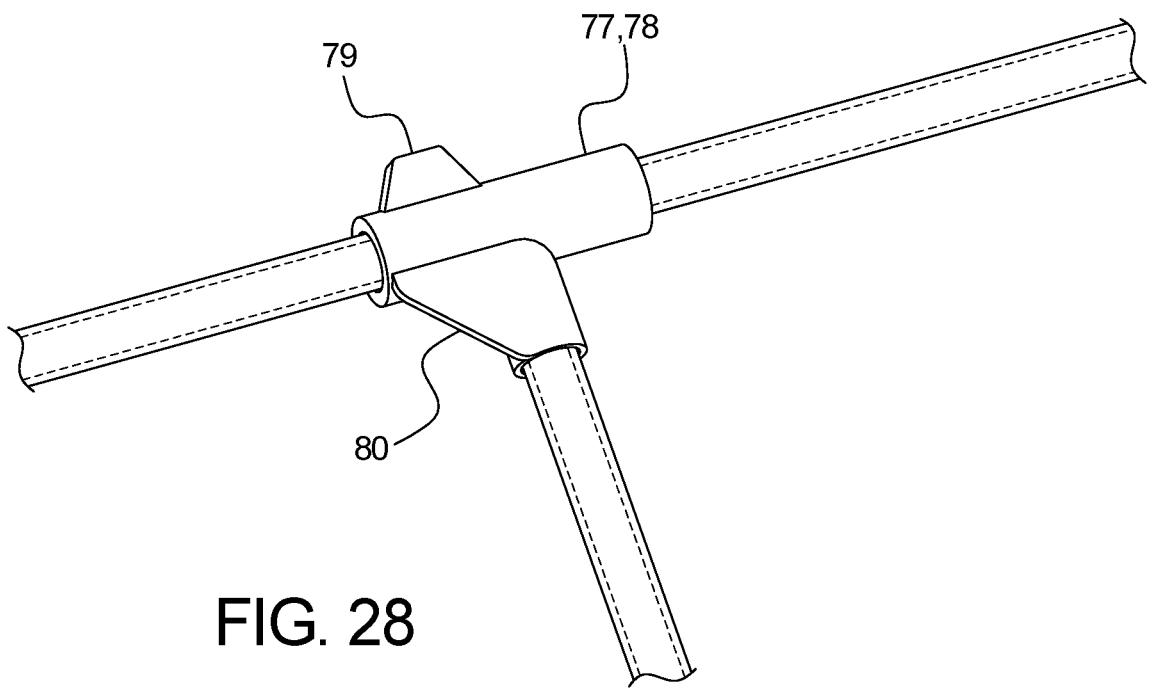
FIG. 28 is directed to a custom fitting with the tubing.

Both Fitting #1 and Fitting #2 are identical, with the exception of color. Fitting #1 77 is colored blue to serve as a visual cue to correspond with the blue color of the Heater Unit, since Fitting #1 is inserted next to or between the Heater Unit's pinch valve(s). Fitting #2 78 is colored white or clear to serve as a visual cue corresponding with the white color of the Control Unit, since Fitting #2 is inserted between the Control Unit's pinch valves. The custom tee fittings contain a trapezoid-shaped protrusion 79 offset only on one side of the tee and not the other side, as shown in FIG. 28.

This protrusion mates with a similarly shaped notch or groove 81 in the interior wall inside the door of the Heater Unit and/or Control Unit. The protrusion and associated notch or groove provide both a visual cue as to the proper orientation of the Tee, as well as a physical barrier to discourage or prevent the tees from being installed in the reverse orientation between the pinch valves, since a normal tee shape would be symmetrical about its center axis. In addition to the aforementioned protrusion, the custom tee fittings contain a triangular gusset on one side of the vertical axis of the tee and not the other side.

A protrusion 82 extends up vertically from the floor of the APD device such that its height exceeds the height of a properly inserted tee fitting which is inserted in a vertical orientation from top to bottom such that the tee rests on a horizontal surface when properly seated. This protrusion extends through the empty space on only the side of the tee fitting opposite from the gusset, such that if the tee fitting were installed in the reverse orientation, the floor protrusion would interfere with the triangular gusset in the tee fitting and thus prevent the tubing set from being installed between or next to the pinch valves.

These two features together, the trapezoidal protrusion (which could be another shape, such as, but not limited to, a rectangular or semi-circular protrusion in an alternative embodiment) and the triangular gusset 80 (which could be another shape in an alternative embodiment, such as, but not limited to, a rectangle, triangle, or semi-circle), along with the corresponding mating features in the APD device hardware, prevent loading the tee fitting in the reverse orientation.

The fitting can be in the shape of an elbow rather than a tee, for Standard model tubing sets which have only one pinch valve in the Heater Unit for replenishing from the Supply Line and which have no Last Fill Line. The other aforementioned features could be similar, including the custom fitting protrusion 79 and gusset 80, as well as the corresponding wall notch or groove 81 and floor protrusion 82 opposite from the gusset.

Figure 29:
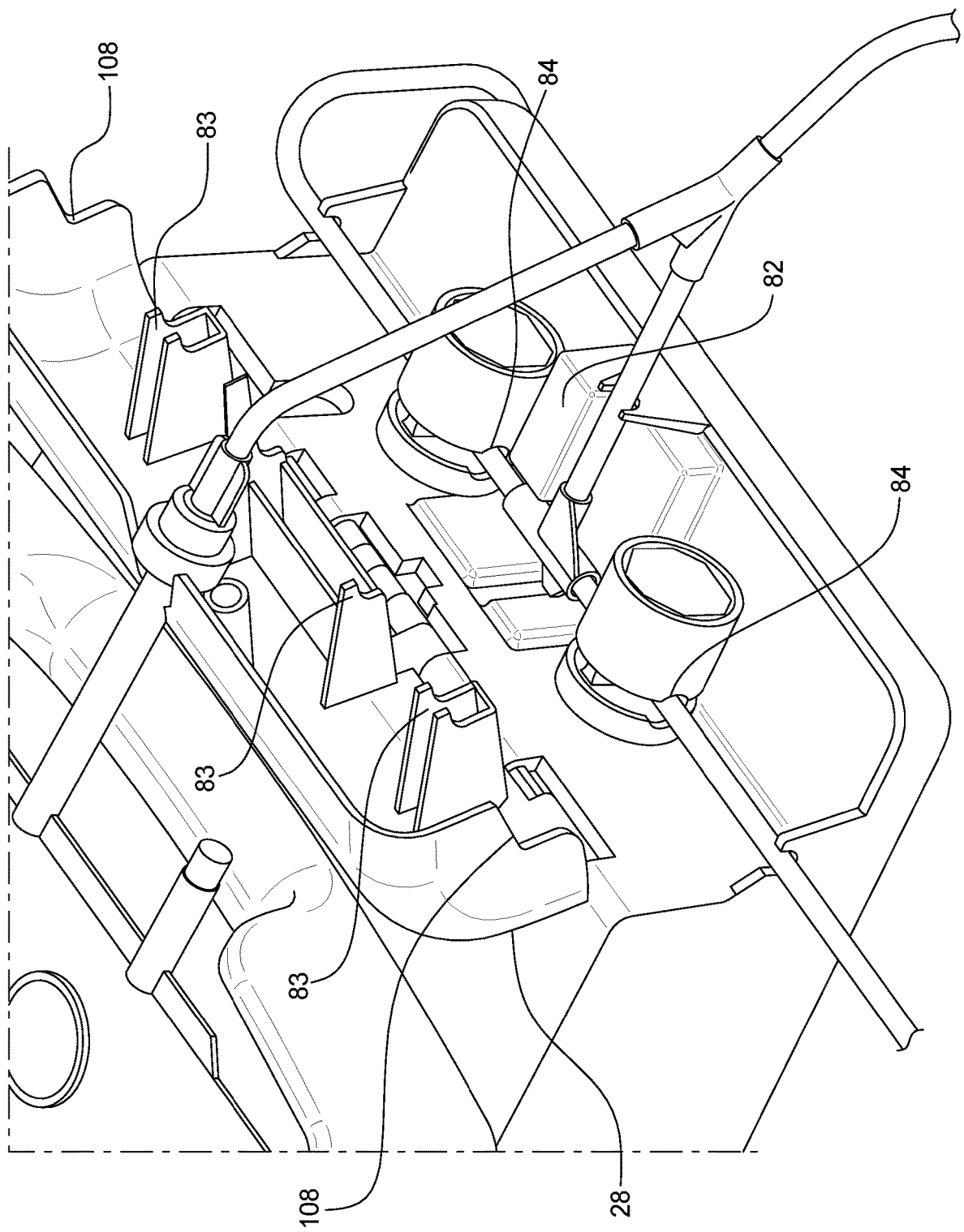
FIG. 29 is directed to heater unit door features to prevent tubing dislodgement.

Both the Heater Unit door and Control Unit doors can contain rib features 83 which would interfere with the triangular gusset 80 if the tee fitting is installed in the reverse orientation when the door is fully closed. As shown in FIG. 29, these door ribs, along with notches 108 in the door, also serve to secure the tubing into the pinch valve jaws and to prevent the tubing from accidentally coming out of the pinch valve jaws 84 during therapy. If the door is not fully closed, or is opened during therapy, a door position sensor 85 may be included which may prevent the user from starting or continuing therapy if the door is not fully closed. An alarm may also be triggered if the door position sensor detects an opened door during disposable tubing setup steps or during active therapy. The graphical user interface touch screen 42 can display pictorial guidance to ensure the user loads the tee fittings in the proper orientation.

The tee fitting for the Heater Unit can have different physical features, such as one or more additional protrusions or notches, or alternatively, could have different shaped protrusions/notches, from the tee fitting for the Control unit. In this embodiment, each of the Heater Unit and Control Unit enclosures contain different mating protrusion or notch features unique to its own tee fitting such that the tee fitting intended for placement in the Heater Unit will not fit into the Control Unit and vice versa.

All of these aforementioned features surrounding the custom fitting and its associated mating parts and UI instructions serve to prevent loading the tubing set in the reverse orientation into either the Heater Unit or the Control Unit's pinch valves. They also serve as free flow prevention, which may reduce the likelihood of unintended Increased Intraperitoneal Volume (IIPV) or overfill of the patient.

The APD device can include three (Standard) or four (Pro) spring-loaded, normally closed solenoid-operated pinch valves 23 to control fluid delivery from source dialysate containers to the patient, and from the patient to the drain destination. Normally closed pinch valves offer benefits to prevent unintended Increased Intraperitoneal Volume (IIPV)/overfill, or unintended draining in the event of loss of power to the pinch valves (fail safe).

This device envisions one normally closed pinch valve 25 to control fluid replenishment from one or more Supply dialysate bags 5 to a Heater dialysate bag 4.

Another optional last fill pinch valve 24 is envisioned for the Pro model to control fluid replenishment from a Last Fill dialysate bag 6, such as icodextrin, to the Heater bag 4. One device configuration (Standard model) may omit the Last Fill valve for patients who use the same dextrose-based fluids for their Last Fill as their other Fill phases and do not require a unique fluid type such as icodextrin for their Last Fill. The Last Fill fluid remains in the patient's abdomen for the long daytime dwell period. Another Patient Fill pinch valve 26 can be included for filling the patient, controlling fluid flow from the Heater Bag 4 which sits on a heated surface 38, to the patient 8. The patient's peritoneal catheter remains below the heater bag for gravity flow.

In addition, one or more pinch valve doors 28 contain mechanical features to prevent accidental tubing removal from the pinch valves, with a door position sensor 85 on each of the Heater Unit door and Control Unit door to ensure the doors remain in the closed position during therapy.

The system can include noise-reducing components, including the doors and foam. The Heater Unit and the Control Unit each have a door 28 covering their respective pinch valves. This door serves to mitigate clicking noise from the solenoid-operated pinch valves when the solenoid activates or deactivates. Additionally, noise dampening foam 86 or other noise dampening materials may be used to line the inside of the doors covering the pinch valve jaws and/or around the body of the pinch valve coil housing area.

The peritoneal dialysis device can include a bag lift assist mechanism 61 that utilizes mechanisms to assist in lifting and/or placing dialysate bags from their storage boxes, which may be close to ground level, to either waist level or approximately eye level for gravity delivery, while minimizing the forces or level of difficulty required from the user setting up the device to prepare for therapy. This may also serve to increase the flow rates while filling the patient 8 from the Heater Bag 4, by increasing the available head height from the Heater Bag to the patient's peritoneal catheter in their abdomen. They may also serve to increase flow rates while replenishing the Heater Bag 4 from either the Supply Bag 5 or from the Last Fill Bag 6.

The APD device envisions one or more spring-loaded mechanical reels with retractable cable(s) to provide lift assistance by hoisting one or more dialysate bags to the preferred height. In this manner, the patient or caregiver may use their body weight to pull the cable down out of the spring-loaded reel, attach one or more bags to the distal end of the cable, and allow the spring tension to assist in raising the bag(s) to the proper height.

Figure 18:
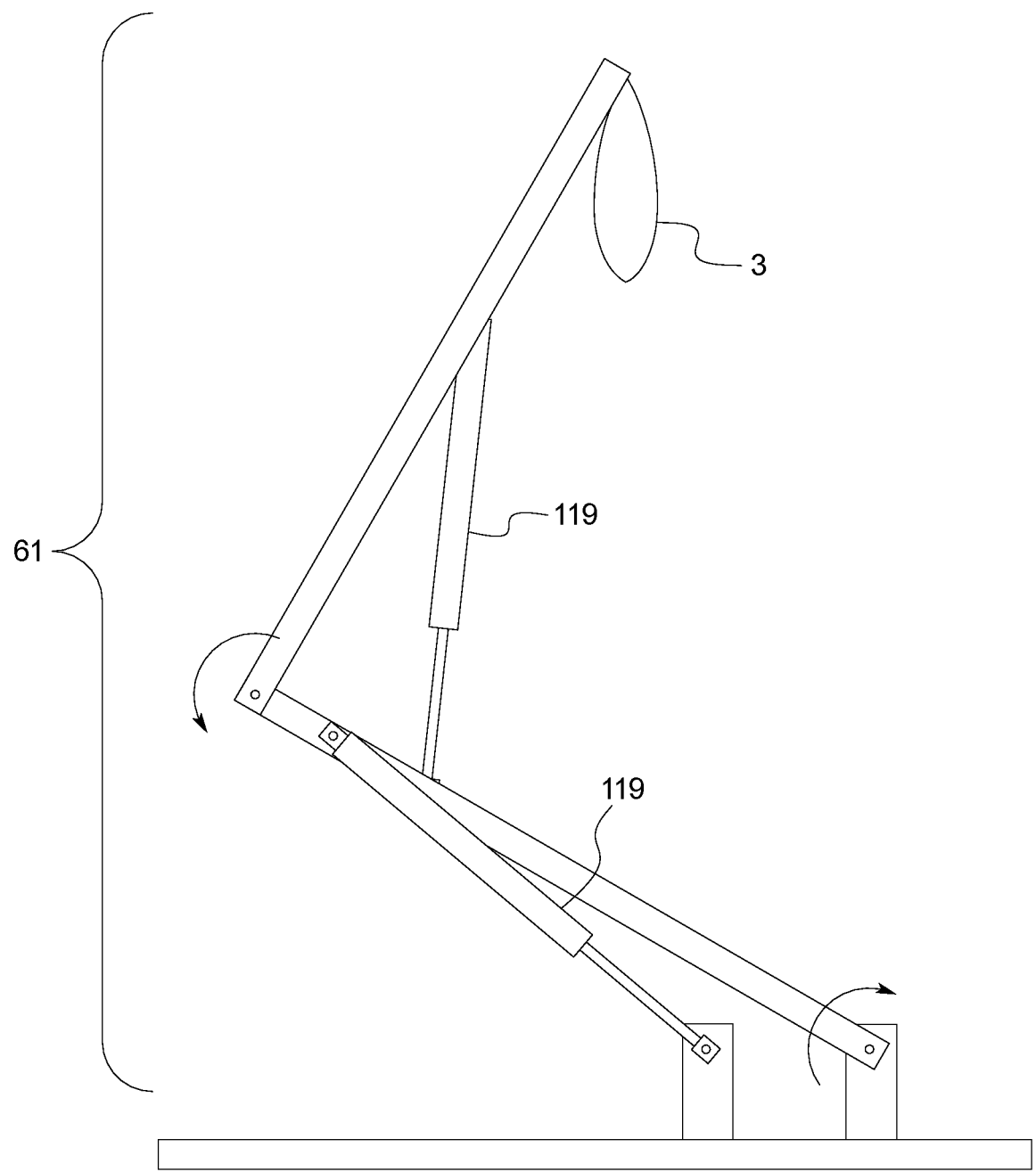
FIG. 18 illustrates the APD device's bag lift assist mechanism with a gas springs or linear actuators used to lift the dialysate bag(s). The arms are connected to each other and to the base support via hinges or pins.

The APD device envisions one or more gas springs 119 or linear actuators are used to rotate one or more arms from a horizontal position towards a more vertical position, whereby the dialysate bag(s) are mounted toward the distal end of one of the arms prior to deploying the arm(s) upward, as shown in FIG. 18. The APD device can include one or more spring-loaded hinges to help extend one or more "arms" from the ground level to the proper height. The bags are envisioned to be mounted toward the distal end of at least one of the arm(s) prior to raising the arm(s).

The APD device can include one or more pulleys used in conjunction with a cable, rope, belt, string, or similar component to raise one or more dialysate bags. The pulleys may be arranged such that pulling the cable a certain amount results in the bag being elevated by that same amount, or in a fashion such that pulling the cable in a distance 2× results in the bag being raised 1×, or similar multiplier which achieves additional mechanical advantage. The user may use his or her body weight to pull down on the cable to lift the dialysate bag(s).

The APD device can include one or more electric motors to pull one or more dialysate bags up to the intended height. The motor type could be a stepper motor, brush DC, brushless, or other motor types. One or more limit switches and/or encoders may be used to automatically stop the motor drive when the bag reaches its intended height.

Figure 19:
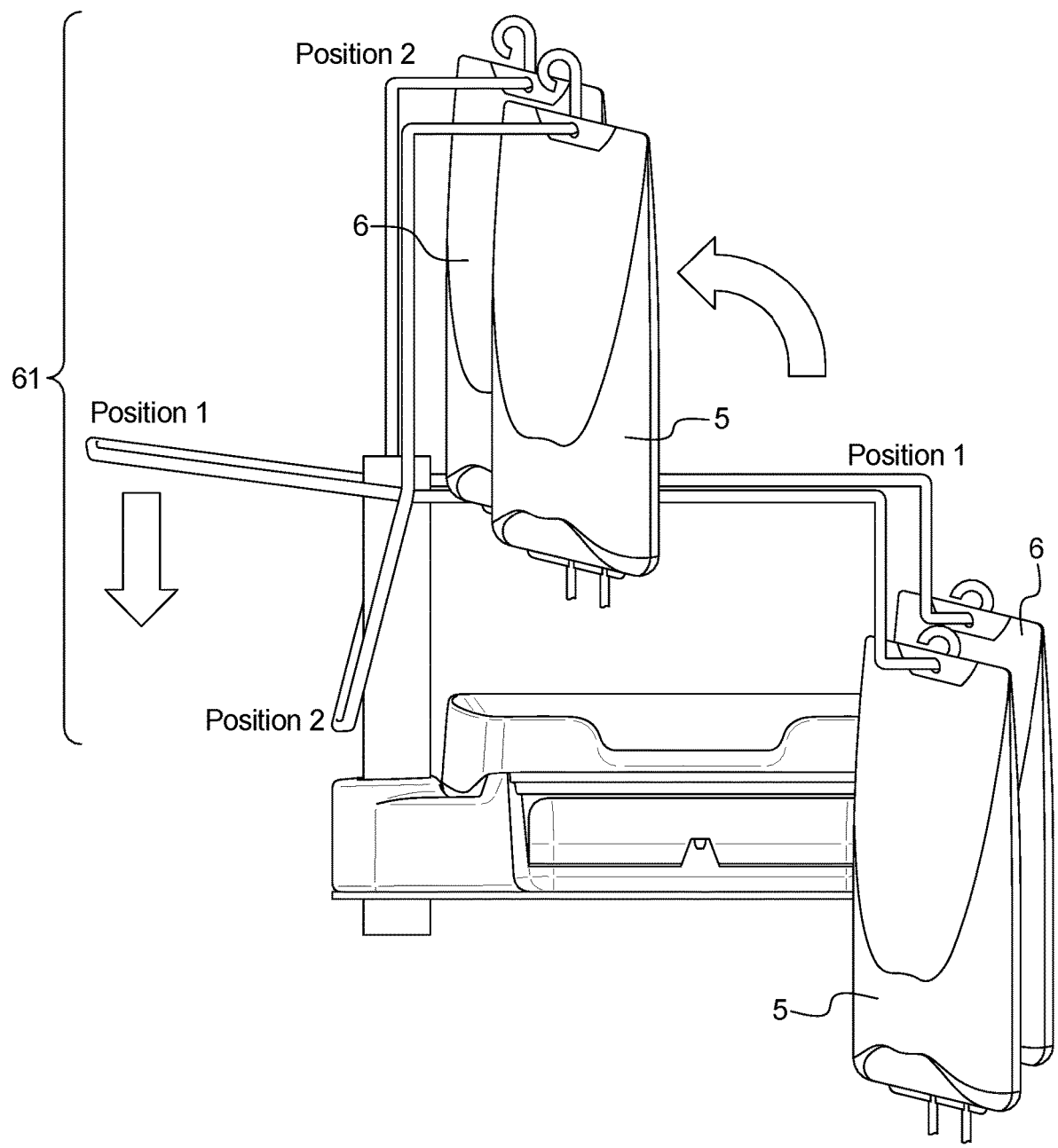
FIG. 19 illustrates the APD device's bag lift assist mechanism with an alternate lever mechanism used to lift the dialysate bag(s), showing the dialysate bags above the height of the APD device's heater plate in their lifted position.

The APD device can include one or more levers used to hoist one or more dialysate bags up to the proper height. The operator may use his or her body weight to actuate the lever(s), although other configurations where the lever is not pulled in a downward direction may be envisioned. The lever could be fitted with a counterweight, if desired. As shown in FIG. 19, the lever mechanism allows the user to use their body weight to pull a handle down, which lifts a supply bag 5 and last fill bag 6 above the top of the heater bag 4 resting on the heater plate 38. This allows gravity to replenish the heater bag from the supply bag and/or last fill bag.

The APD device can include a ladder-like structure which uses a flexible strap, cable, or rope to hoist one or more ladder segments to a higher position, whereby the dialysate bag(s) are mounted at or near the top of one of the ladder. Pulling on the strap causes one or more ladder segments to be raised in a similar manner as a common household extension ladder behaves. The APD device can include one or more manual crank mechanisms, which may or may not be geared to obtain additional mechanical advantage, to raise or lower one or more arms or similar structure in a rotating or linear fashion.

The APD device can include one or more screw mechanisms, such as a ball screw or lead screw or other screw mechanism, to raise and lower one or more dialysate bags by turning a nut on the screw, whereby the dialysate bags are hung from or sitting on structure that is mounted to the nut.

The APD device can include one or more linear motion rails with either cam followers or traveling car(s) with bushings or bearings that keep the car(s) gliding along the rail in a linear fashion up and down the rails, such that the dialysate bag(s) are raised or lowered with the linear motion translational elements.

The APD device can include two or more telescoping tubes whereby each tube fits snugly inside the next larger tube and whereby the dialysate bag(s) are affixed to or mounted onto structure that is attached to one of the telescoping tubes. The tubes may be round, square, or any other cross-sectional shape. This may be used to aide in dialysate bag height assist and/or for device portability, in the event that the user would like to collapse the PD device to transport it to another location. The telescoping tubes can be spring loaded in the upward position, whereby the user could use their body weight to pull them down to a lower position and thus hang or mount the bags more easily, before releasing a pin or other mechanism to allow the tubes to extend again.

The APD device can include a scissor lift to raise or lower the dialysate bags. The scissor lift could be further augmented by the use of a crank, motor, and/or screw mechanism to assist in lifting the platform or other structure which the dialysate bag(s) reside upon or hang from.

The APD device can include one or more hydraulic or pneumatically driven cylinder(s) or other structure in such a way that the dialysate bag(s) are raised or lowered by increasing or decreasing the pressure within the cylinder.

The APD device can include one or more one or more counterweights may be used to offset the weight of dialysate bag(s) via the use of a pulley and cable or similar mechanism. The counterweights could be swappable in different weight sizes to correspond with the weight of the dialysate bag(s).

The APD device can include one or more APD device user interface screens includes a colored icon, or image which matches the color of one or more elements of the dialysate solution container and/or the dialysate solution container's shipping box for a given dialysate concentration. One current convention uses the following color scheme: yellow for 1.5% dextrose, green for 2.5% dextrose, red for 4.25% dextrose, and purple for 7.5% icodextrin. This color may be the color of the box's adhesive tape, with each color corresponding to a unique dialysate solution concentration.

Figures 20, 21:
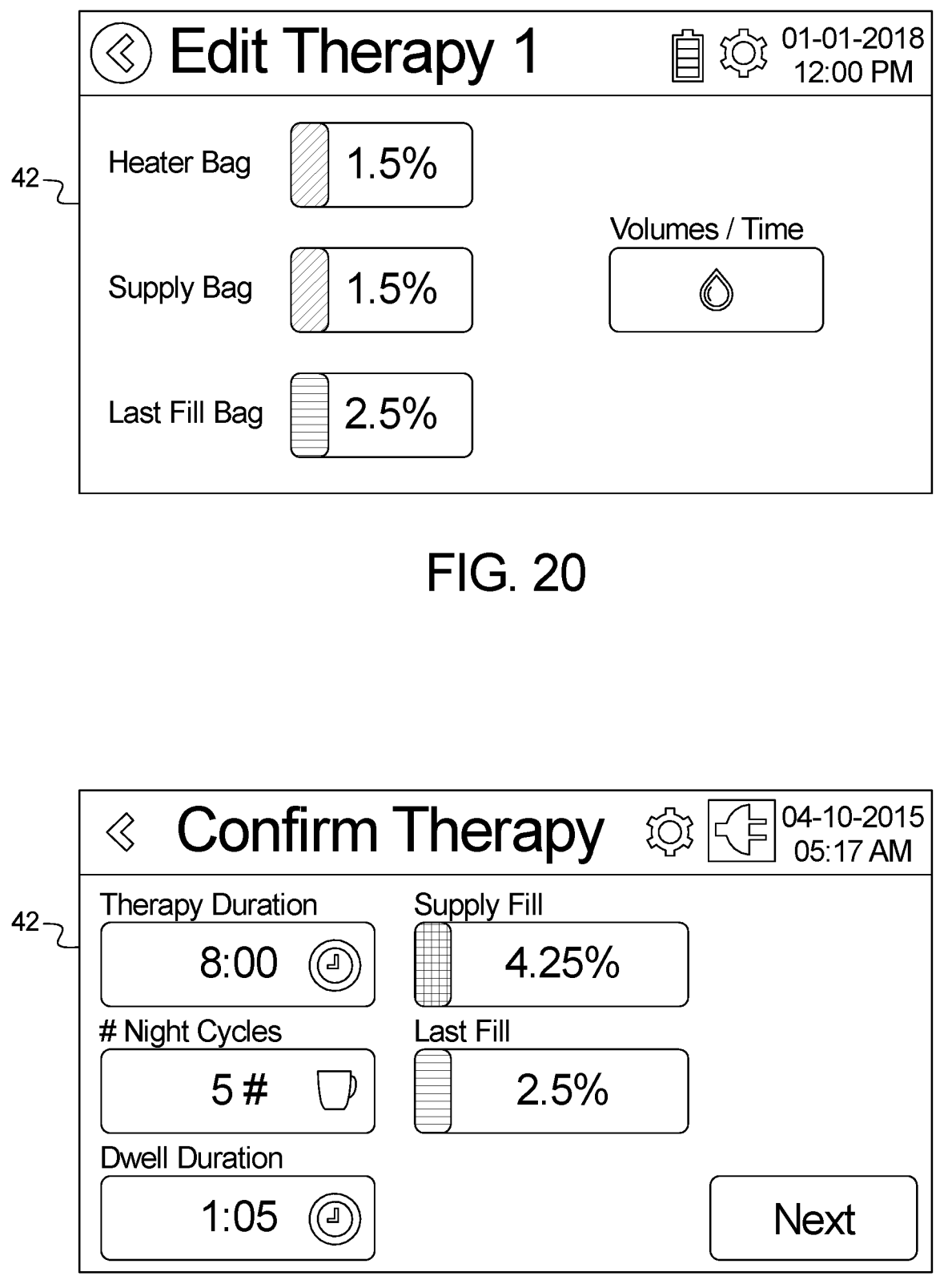

Alternatively, the color on the user interface for a given dialysate concentration could correspond to the color of one or more molded or printed elements of the dialysate solution bag assembly, such as a connector, access port, printed labeling, removable cap, and/or tip protector. The color-matched screens could include therapy programming screens as in FIG. 20 and/or therapy confirmation screens as in FIG. 21.

The user interface can include a color touch screen 42 (e.g., user interface) in the Control Unit. A single power button serves to power on/off the device. It also serves as a therapy pause button to close off fluid flow to or from the patient and/or from solution bags. The power button slowly blinks via integrated LED when powered on and/or during therapy to help the user know that the device is still properly functioning, even, for instance, when it may not be obvious that therapy is running, such as during a Dwell phase. Remaining battery life is conveyed graphically on the touch screen 42. Therapy progress is indicated by graphical and text-based guidance. Icons and graphical sketches or pictures help guide the user through therapy setup, teardown, monitoring, and troubleshooting alarm conditions. This helps facilitate illiterate or low literacy users to be able to perform APD therapy.

The user interface can allow the user to program a therapy in a manner which automatically adapts to the Total Therapy method or Number of Cycles method. If the user directly enters the total therapy volume, the system automatically transitions to Total Therapy method and calculates the number of cycles. In one embodiment, the formula for calculating number of cycles is:

$$\frac{\text{(Total therapy volume} - \text{last fill volume)}}{\text{Cycle fill volume}}$$

The number of cycles may be rounded up to the nearest integer if the decimal portion exceeds 0.85.

Alternatively, if the user directly enters the number of cycles, the system automatically transitions to the Number of Cycles method and calculates the total therapy volume. In one embodiment, the formula for calculating total therapy volume is:

Total Therapy Volume=(Number of cycles)×(Cycle fill volume)+Last Fill Volume

Similarly, if the user directly enters the total therapy duration, the system automatically transitions to the Total Therapy method and calculates the per-cycle dwell duration. In one embodiment, the formula for calculating per-cycle dwell duration is:

$$\text{Cycle dwell duration} = \frac{\text{total therapy duration} - \text{total fill duration} - \text{total drain duration}}{\text{Number of cycles}}$$

where $$\text{Total drain duration} = \frac{\text{(Number of cycles)} \times \text{(Cycle fill volume} + \text{cycle } UF \text{ volume)} + \text{Target initial drain volume}}{\text{Estimated drain flow rate}}$$

where $$\text{Cycle } UF \text{ volume} = \frac{\text{total } UF \text{ target}}{\text{Number of cycles}}$$

where the total UF target is the user-entered total ultrafiltration target for the entire therapy. The system may omit cycle UF volume from the total drain duration calculation.

Alternatively, if the user directly enters the per-cycle dwell duration, the system automatically transitions to the Number of Cycles method and calculates the total therapy duration. In one embodiment, the formula for calculating total therapy duration is:

Total therapy duration=cycle dwell duration×Number of cycles+total fill duration+total drain duration If the user started out directly programming a parameter that enables the Total Therapy method (i.e. Total Therapy Volume or Total Therapy Duration), then directly edits a parameter that enables the Number of Cycles method (i.e. Number of Cycles or Cycle Dwell Duration), then the previously directly entered values (i.e. Total Therapy Volume and Total Therapy Duration) immediately become calculated values.

Figure 22:
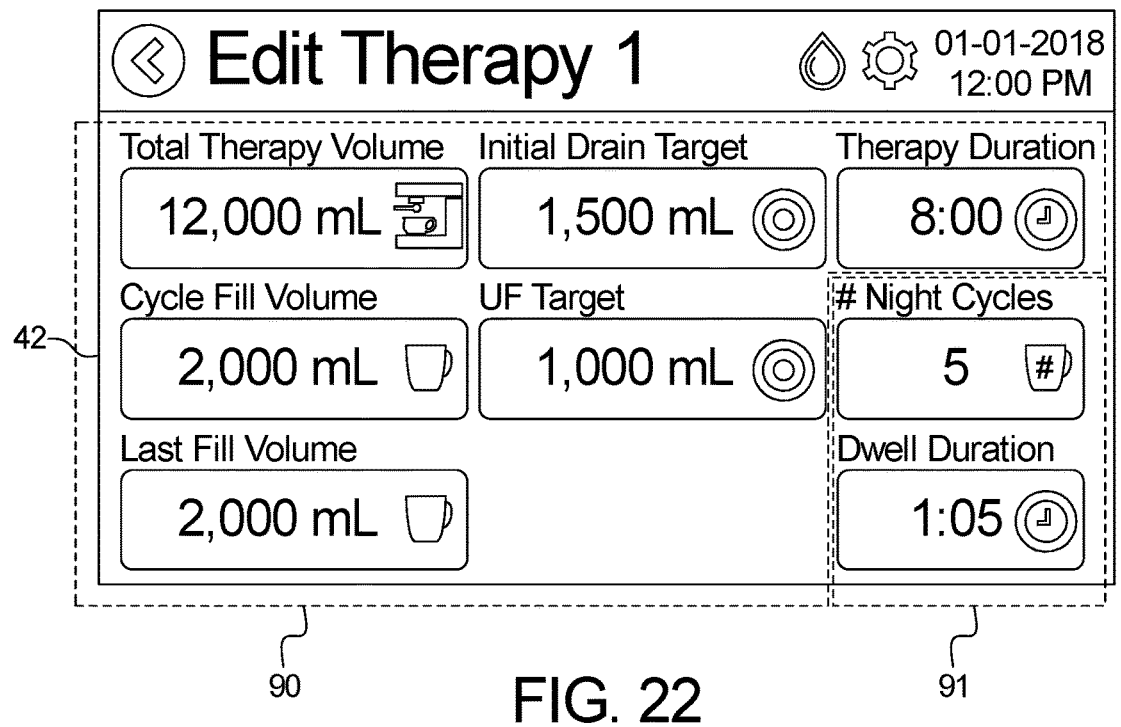
FIG. 22 illustrates a therapy programming screen using the Total Therapy Method.
Figure 23:
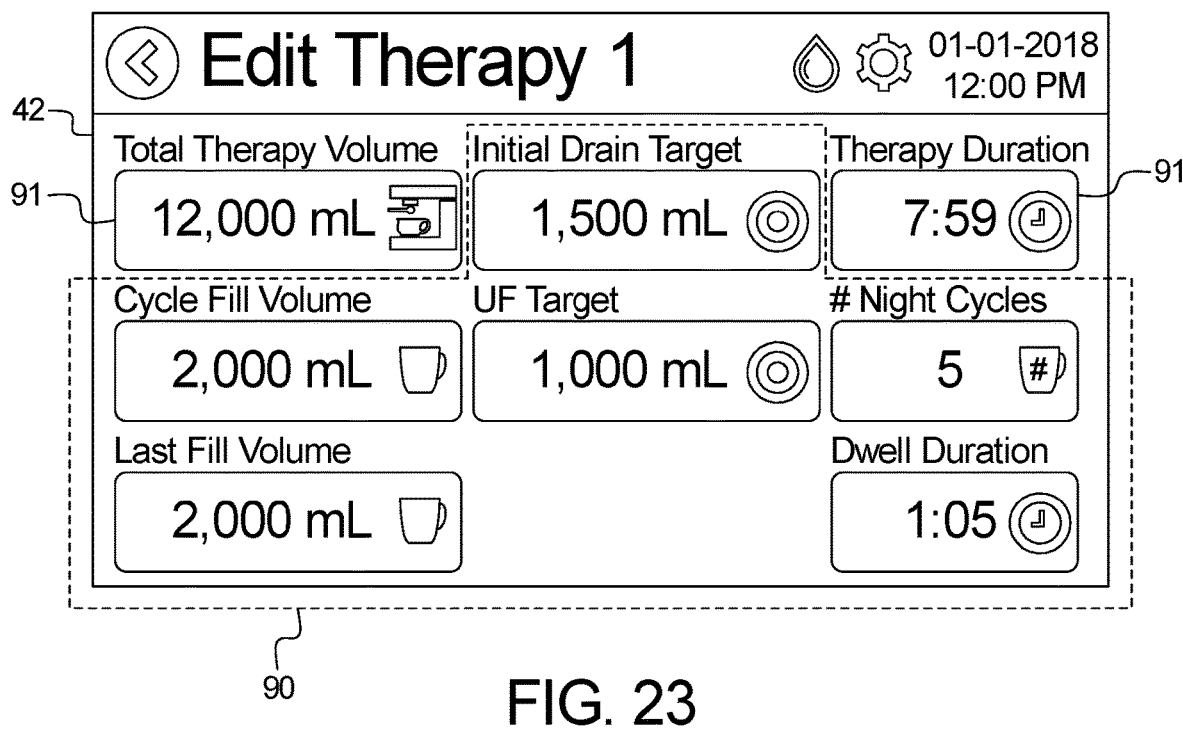
FIG. 23 illustrates a therapy programming screen using the Number of Cycles method.

A screen depicting programming the therapy parameters using the Total Therapy Method is displayed in FIG. 22. A screen depicting programming the therapy parameters can use the Number of Cycles Method, as shown in FIG. 23. In both programming methods, in a preferred embodiment, the user-entered parameters 90 are shown with white text on a dark grey background, while the calculated parameters 91 are shown with dark text on a light grey background.

Figure 24:
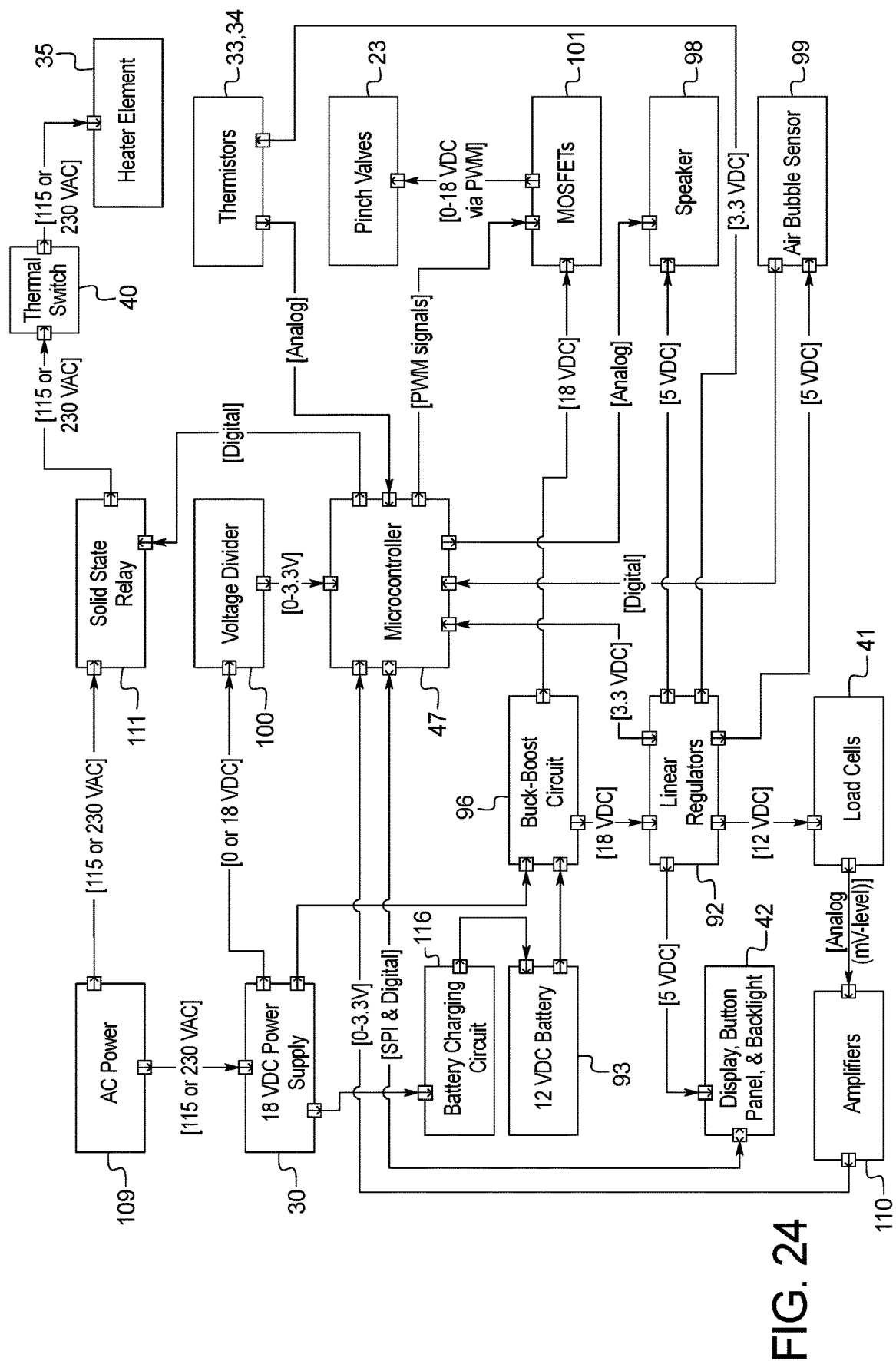
FIG. 24 illustrates the electrical power distribution block diagram.
Figure 25A:
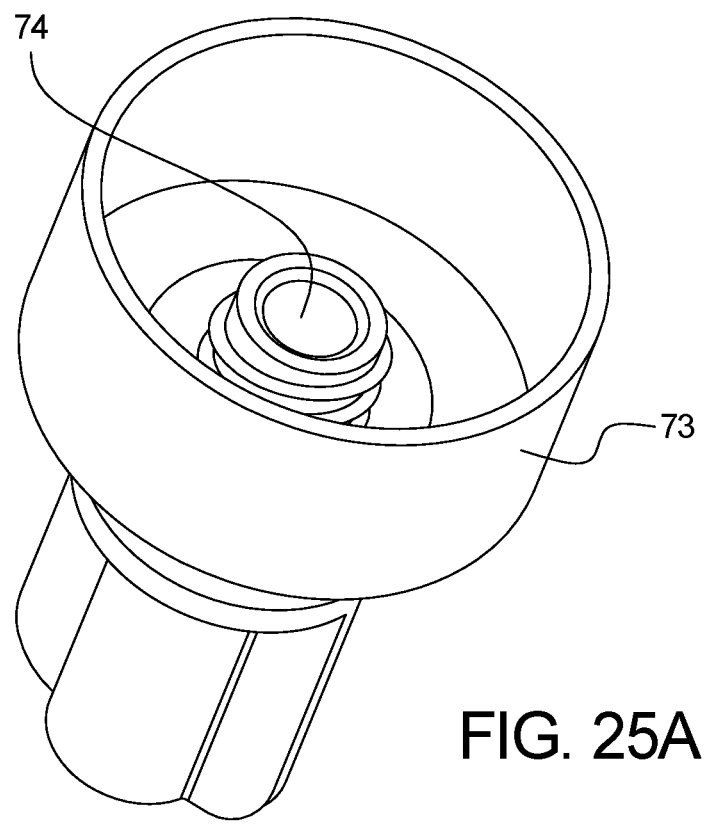
FIGS. 25A-25C are directed to the shrouded female Luer connector.
Figure 25B:
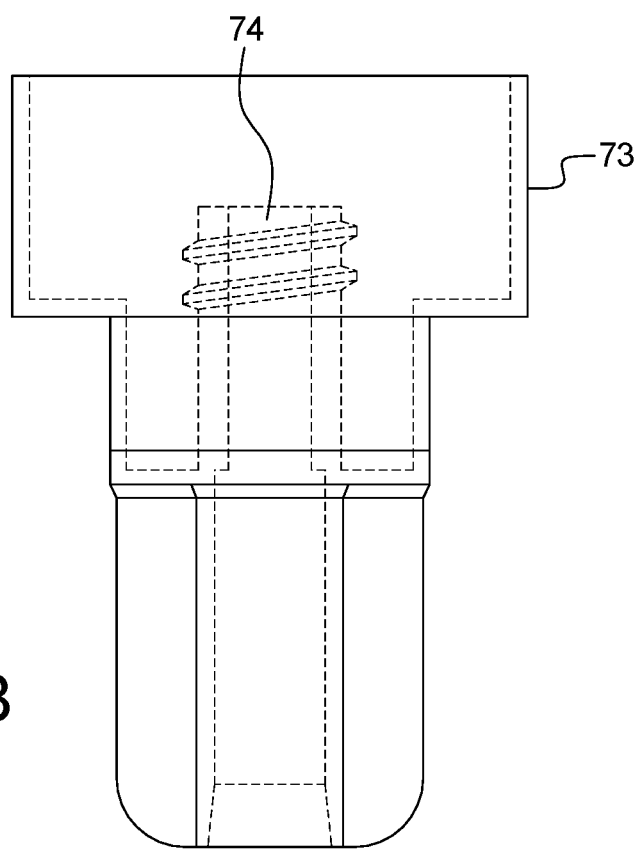
Figure 25C:
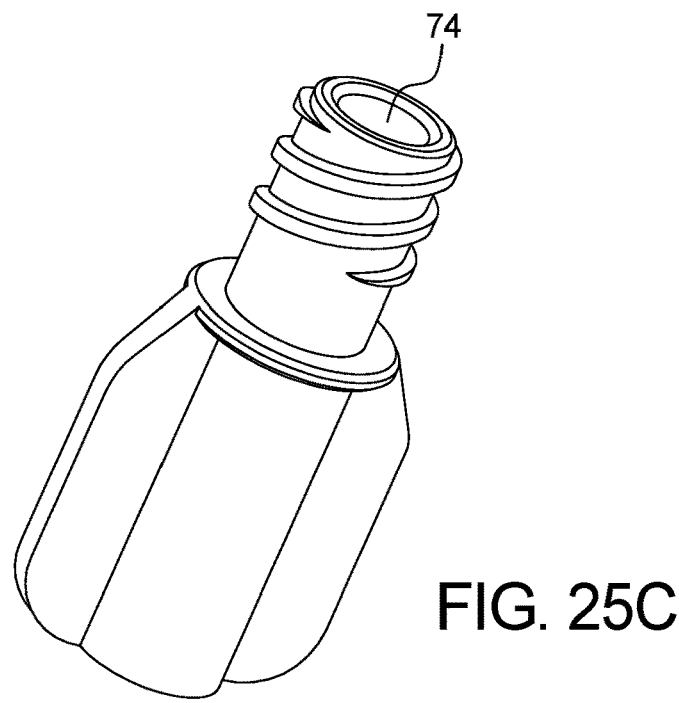
Figure 26:
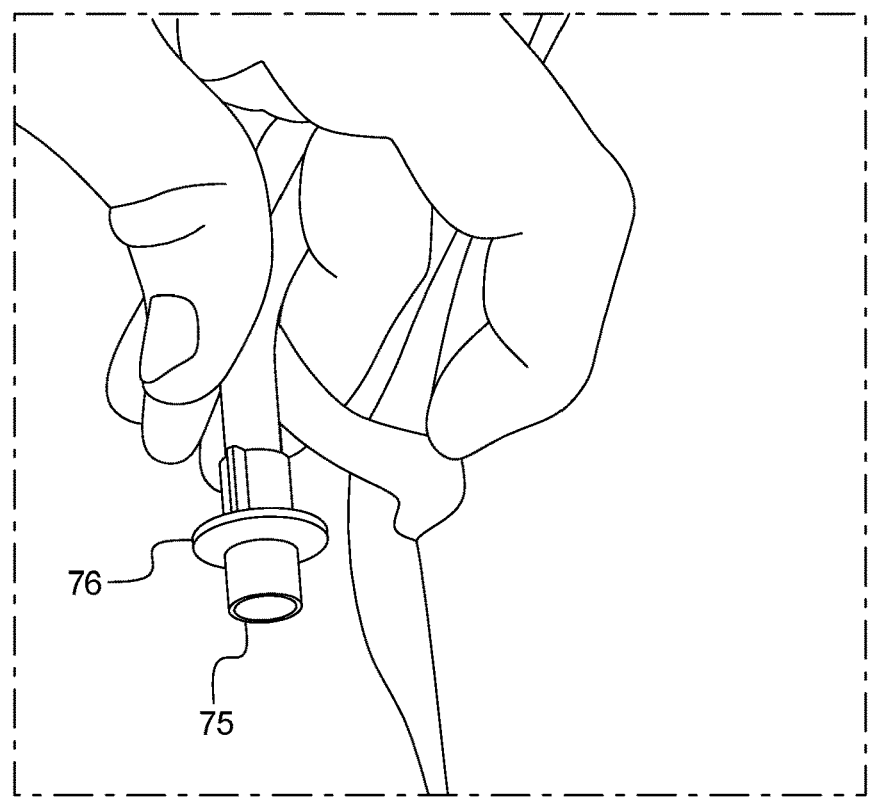
FIG. 26 is directed to the shrouded male Luer solution bag connector.
Figure 27:
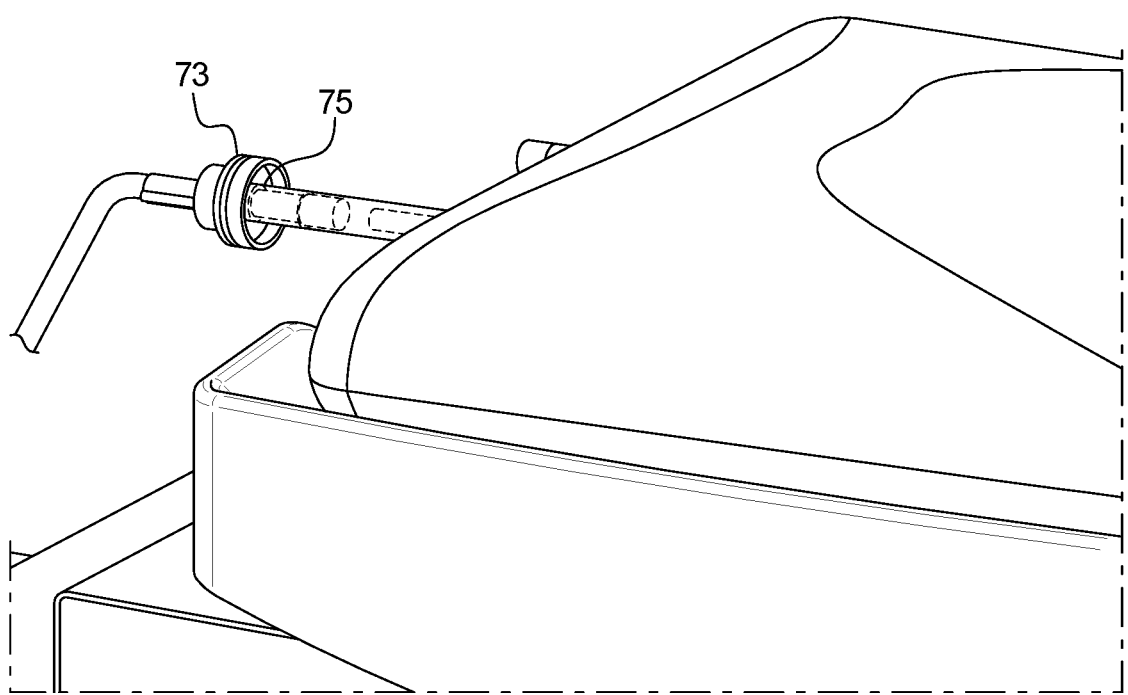
FIG. 27 is directed to a shrouded female Luer connected to a shrouded male Luer of the solution bag.

The power management system is shown in FIG. 24, wherein the APD system uses a heater element 35 powered by AC power 109 and switched via one or more solid state relays 111. An AC to DC power supply 30 provides 18 VDC power to the remaining components.

The pinch valves 23 are driven by the 18 VDC power supply 30 which is modulated by PWM control of MOSFETs 101 via the main microcontroller 47 to reduce the power draw after initially opening a given valve. The pinch valves are designed for 12 VDC nominal voltage, but are unable to open the jaws 84 at that voltage without tubing 7 installed in the jaws. By energizing them with an 18 VDC "spike" for short periods, such as 100 ms in a preferred embodiment, followed by a hold at a lower average "hold" voltage such as 5 VDC via PWM, the pinch valves are able to open their jaws regardless of tubing installed, to facilitate the user loading the disposable tubing set. During the initial spike period for one pinch valve, another pinch valve cannot be commanded open until the first pinch valve is in its hold phase. This allows the system to use a DC power supply rated at a lower wattage than if the system were to need to deliver higher spiking power levels to two or more pinch valves at the same time.

Load cells 41 are powered by a 12 VDC linear regulator 92 fed by the 18 VDC power supply 30, with the millivolt output signals boosted by amplifiers 110. Additional voltage converters are included on one or more circuit boards to step down the 18 VDC power to 5 VDC and/or 3.3 VDC to drive additional electronic components including the microcontroller 47, display 42, speaker 98, and/or air bubble sensor 99. A 12 VDC battery 93 is included for battery backup purposes.

Both the 12 VDC battery output and the 18 VDC power supply output can be routed through a buck-boost circuit 96 to ensure output voltage is 18 VDC, regardless of whether the system is being driven by AC power or battery power. During AC power outage conditions, in one embodiment, the system detects this condition by monitoring the DC output voltage from the AC to DC power supply 30 via voltage divider 100 from the DC power supply to the microcontroller 47 and stops heating dialysate fluid in the Heater Bag if the optional battery-powered heater boost circuit is not installed. At this point, the system continues operating the microcontroller 47, speaker 98, pinch valves 23, load cells 41, thermistors 33 and 34, air bubble sensor (if present) and all other electronics and components needed to continue running therapy without heating. The system monitors the Heater Bag 4 temperature via heater bag thermistors 34 during power outage conditions. As long as the heater bag temperature remains at or above 25° C. or other suitable minimum temperature for delivery, which could be fixed in one embodiment or could be programmable within a specified range such as 25° C. to 35° C. in another embodiment, the therapy is allowed to continue filling the patient during fill phases. Once heater bag temperature falls below the acceptable minimum delivery threshold, the system stops filling, alarms (audible and visual), and notifies the patient that AC power is out. If power is restored before the battery level falls below the critical level required to maintain the microcontroller, display, and speaker, then therapy may resume. If AC power remains out beyond that point, the system alarms, notifies the user, and shuts down therapy.

A secondary heater boost circuit can boost the 12 VDC to a higher voltage, such as 24 VDC, 36 VDC, or 48 VDC to power the heater element 35 on battery power. The primary buck-boost circuit as described above continues to boost the 12 VDC battery voltage to 18 VDC to drive the pinch valves, while stepped-down voltages power the microcontroller, speaker, load cells, thermistors, air bubble sensor (if present) and all other electronics and components needed. This allows the system to continue running therapy on battery power, including heating the Heater Bag.

As mentioned above, aspects of the systems and methods described herein are controlled by one or more controllers. The one or more controllers may be adapted to run a variety of application programs, access and store data, including accessing and storing data in the associated databases, and enable one or more interactions as described herein. Typically, the controller is implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a central control processing system utilizing a central processing unit (CPU), memory and an interconnect bus. The CPU may contain a single microprocessor, or it may contain a plurality of microprocessors for configuring the CPU as a multi-processor system. The memory may include a main memory, such as a dynamic random access memory (DRAM) and cache, as well as a read only memory, such as a PROM, EPROM, FLASH-EPROM, or the like. The system may also include any form of volatile or non-volatile memory. In operation, the memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller. For example, the one or more controllers may include a graphics subsystem to drive the output mechanism. The links of the peripherals to the system may be wired connections or use wireless communications.

Although summarized above as a PC-type implementation, those skilled in the art will recognize that the one or more controllers also encompasses systems such as host computers, servers, workstations, network terminals, and the like. Further one or more controllers may be embodied in a device, such as a mobile electronic device, like a smartphone or tablet computer. In fact, the use of the term controller is intended to represent a broad category of components that are well known in the art.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as the memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, flash memory, microSD card, USB thumb drive stick, any other memory chip or cartridge, or any other medium from which a controller can read programming code and/or data. Many of these forms of computer readable media may be involved in carrying one or more sequences of one or more instructions to a processor for execution.

It should be noted that various changes and modifications to the embodiments described herein will be apparent to those skilled in the art. Such changes and modifications may be made without departing from the spirit and scope of the present system and without diminishing its attendant advantages. For example, various embodiments of the systems and methods may be provided based on various combinations of the features and functions from the subject matter provided herein.

We claim:

1. A peritoneal dialysis system comprising:
   a disposable tubing including a heater line tube for connecting to a heat dialysate bag, and a supply line tube for connecting to a supply dialysate bag;
   a female fitting connected to a first end of the heater line tube, wherein the female fitting configured to mate with a male fitting of the heat dialysate bag, wherein the female fitting includes a female shroud extending above a surface of the fluid path of the female fitting,
   wherein when the female fitting mates with the male fitting, the female shroud is positioned around a male shroud of the male fitting of the heat dialysate bag, wherein a fluid path of the male fitting is recessed within the male shroud,
   wherein when the female fitting mates with the male fitting, a circular disc extending from the male shroud is positioned within the female shroud;
   a heater unit, wherein the heater unit includes a heater bag enclosure for placement of the heat dialysate bag in contact with a heat plate, wherein the heater unit includes a tube housing; and
   a first junction connecting the heater line tube and the supply line tube, wherein the tube housing of the heater unit includes the first junction.

2. The system of claim 1, further comprising a second junction fitting connecting the supply line tube and a first arm of the first junction fitting, wherein the second junction fitting engages with a groove within the tube housing of the heater unit, wherein engagement with the groove properly orients the supply line tubing within the tube housing of the heater unit.

3. The system of claim 2, wherein when the second junction fitting is engaged with the groove of the tube housing of the heater unit, the supply line tube is positioned within a first pinch valve.

4. The system of claim 2, wherein a protrusion extends outward from the second junction fitting, wherein the protrusion engages with a groove within the tube housing of the heater unit, wherein engagement of the protrusion within the groove properly orients the supply line tubing within the heater unit.

5. The system of claim 4, wherein when the protrusion engages with a groove within the heater unit, the supply line tube is positioned within a first pinch valve.

6. The system of claim 4, wherein when the protrusion engages with a groove within the heater unit, a last fill bag tubing is positioned within a second pinch valve.

7. The system of claim 1, wherein the system does not include a disposable cassette.

8. The system of claim 1, wherein the supply line tubing connects to at least one elevated dialysate bag positioned atop an elevated shelf, wherein the elevated dialysate bag is positioned above the heater unit.

9. The system of claim 1, further comprising a drain container positioned below the heater unit, wherein the patient line tubing connects the patient to the drain container.

10. The system of claim 1, further comprising a controller coupled to a memory, wherein the memory is configured to store program instructions executable by the controller, wherein in response to executing the program instructions, wherein the controller is in communication with the heater unit, wherein the controller is configured to control the heater unit.

11. The system of claim 10, wherein the controller is configured to control a temperature of the heat plate.

12. The system of claim 10, wherein the controller is configured to control at least one pinch valve within the heater unit to control the flow of fluid through the supply line tube and the heater line tube, wherein the pinch valve is activated by a solenoid.

13. The system of claim 1, wherein an electrically insulated polyamide film is positioned between the heat plate and a heater element.

14. The system of claim 1, wherein the heater unit includes at least one pinch valve movable, via a solenoid, between an open valve position and a closed valve position, wherein the open valve position allows fluid flow from the supply dialysate bag, wherein the closed valve position prevents fluid flow from the supply dialysate bag, wherein the controller controls the position of the pinch valves.

15. The system of claim 1, wherein the tube housing includes a second junction fitting including a heater floor projection having a corner, wherein the second junction fitting is a T-junction, wherein the T-junction includes a heater gusset between a first arm and a second arm of the T-junction, wherein the first arm is perpendicular to the second arm, wherein when the T-junction engages with the second junction fitting in the tube housing, the second arm and the third arm of the T-junction are adjacent to the corner of the heater floor projection, wherein the heater floor projection prevents improper alignment of the second junction fitting.

16. The system of claim 1, wherein the heater unit includes a load cell in communication with the controller, wherein the controller calculates the fluid volume delivered to the patient based on data from the load cell.

17. The system of claim 1, wherein the system includes a drain unit for receiving fluid from a patient, wherein the drain unit includes a load cell in communication with the controller, wherein the controller calculates the fluid volume exiting the patient based on data from the load cell.

18. The system of claim 1, further comprising a control unit including a user interface in communication with a controller, and a controller tube housing including at least two pinch valves, wherein the controller tube housing receives the heater tube line, wherein a patient line and a drain line exit the controller tube housing, wherein the controller controls the pinch valves for controlling the fluid flow within the heater line tube, the patient line tube, and the drain line tube.

19. The system of claim 18, further comprising a third junction for connecting the heater line tube, the drain line tube, and the patient line tube, wherein the controller tube housing includes a third junction fitting including a control floor projection having a corner, wherein the third junction is a T-junction, wherein the T-junction includes a control gusset between a first arm and a second arm of the T-junction, wherein the first arm is perpendicular to the second arm, wherein when the T-junction engages with the second junction fitting in the controller tube housing, the second arm and the third arm of the T-junction are adjacent to the corner of the control floor projection, wherein the control floor projection prevents improper alignment of the third junction fitting.

20. The system of claim 1, further comprising a control unit including a controller, a user interface in communication with the controller, a control housing, and at least two pinch valves within the control housing, wherein the heater line enters the control housing, wherein a patient line and a drain line exits the control housing, wherein the fluid flow of the heater line and the patient line are controlled by the controller via the pinch valves.

* * * * *